US005653718A

United States Patent [19]

Yoon

[11] Patent Number: 5,653,718
[45] Date of Patent: Aug. 5, 1997

[54] CANNULA ANCHORING SYSTEM

[76] Inventor: InBae Yoon, 2101 Highland Ridge Dr., Phoenix, Md. 21131

[21] Appl. No.: 243,493

[22] Filed: May 16, 1994

[51] Int. Cl.$^6$ .................................................. A61M 25/00
[52] U.S. Cl. ........................ 606/148; 606/185; 604/174; 604/280
[58] Field of Search ...................... 128/751, 752, 128/753, 754; 604/95, 158, 162, 163, 164, 165, 170, 272, 274, 280, 169, 174, 175, 178; 606/167, 171, 185, 148

[56] References Cited

U.S. PATENT DOCUMENTS

| | | |
|---|---|---|
| 2,670,735 | 3/1954 | Brody . |
| 3,039,468 | 6/1962 | Price . |
| 3,253,594 | 5/1966 | Matthews et al. . |
| 3,459,175 | 8/1969 | Miller . |
| 3,613,684 | 10/1971 | Sheridan . |
| 3,817,251 | 6/1974 | Hasson . |
| 3,952,742 | 4/1976 | Taylor . |
| 4,164,943 | 8/1979 | Hill et al. . |
| 4,655,752 | 4/1987 | Honkanen et al. . |
| 4,985,033 | 1/1991 | Boebel et al. . |
| 5,002,557 | 3/1991 | Hasson . |
| 5,009,643 | 4/1991 | Reich et al. . |
| 5,073,169 | 12/1991 | Raiken . |
| 5,122,122 | 6/1992 | Allgood . |
| 5,137,520 | 8/1992 | Maxson et al. . |
| 5,147,316 | 9/1992 | Castillenti . |
| 5,176,648 | 1/1993 | Holmes et al. . |
| 5,176,697 | 1/1993 | Hasson et al. . |
| 5,215,531 | 6/1993 | Maxson et al. . |
| 5,217,441 | 6/1993 | Shichman . |
| 5,217,451 | 6/1993 | Freitas . |
| 5,222,508 | 6/1993 | Contarini . |
| 5,226,890 | 7/1993 | Ianniruberto et al. . |
| 5,232,451 | 8/1993 | Freitas et al. . |
| 5,234,455 | 8/1993 | Mulhollan . |
| 5,248,298 | 9/1993 | Bedi et al. . |
| 5,257,973 | 11/1993 | Villasuso . |
| 5,257,975 | 11/1993 | Foshee . |
| 5,258,003 | 11/1993 | Ciaglia et al. . |
| 5,263,939 | 11/1993 | Wortrich . |
| 5,267,960 | 12/1993 | Hayman et al. .......................... 604/106 |
| 5,267,968 | 12/1993 | Russo . |
| 5,267,969 | 12/1993 | Hirsch et al. . |
| 5,267,970 | 12/1993 | Chin et al. . |
| 5,271,380 | 12/1993 | Riek et al. . |
| 5,273,545 | 12/1993 | Hunt et al. . |
| 5,279,564 | 1/1994 | Taylor . |
| 5,279,575 | 1/1994 | Sugarbaker . |
| 5,284,130 | 2/1994 | Ratliff . |
| 5,284,474 | 2/1994 | Adair . |
| 5,290,249 | 3/1994 | Foster et al. . |

OTHER PUBLICATIONS

Ethicon and You. The Ultimate Surgical Team (Feb. 24, 1992) pp. 10 and 11, Author unknown.

Primary Examiner—Guy V. Tucker

[57] ABSTRACT

A cannula anchoring system for anchoring a cannula in a cavity wall includes a cannula adapted to be inserted through the cavity wall and having a lumen for communication with the cavity and one or more tissue penetrating members carried by the cannula and movable between non-exposed, retracted positions and exposed extending positions where the tissue penetrating members penetrate the cavity wall adjacent the cannula to anchor the cannula therein. The anchoring system can be used for stabilizing the cannula longitudinally and in desired angular orientations, manipulating for lifting the cavity wall and/or in combination with lengths of suture material passed through or attached to the tissue penetrating members for puncture site closure.

27 Claims, 17 Drawing Sheets

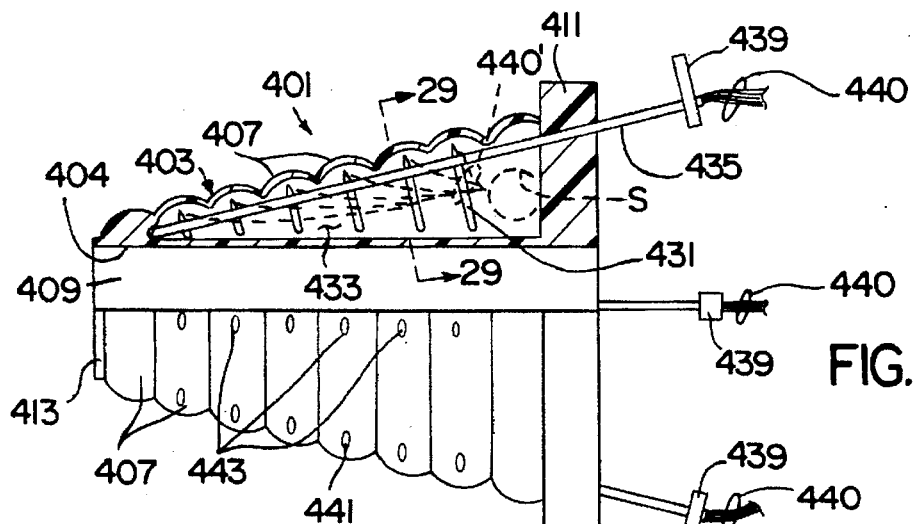
FIG. 25
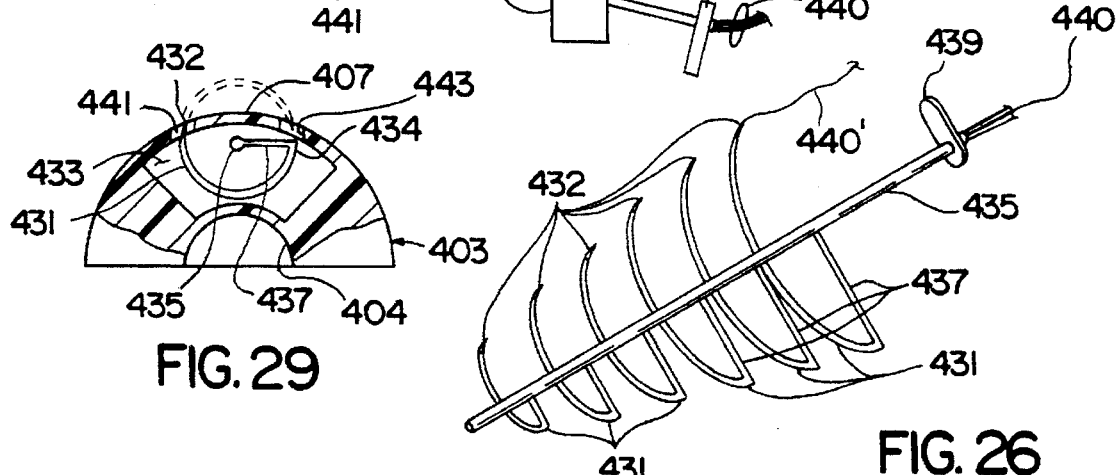
FIG. 29
FIG. 26
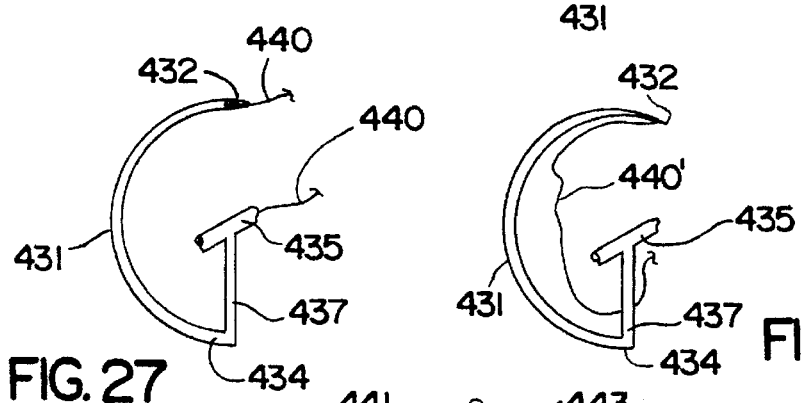
FIG. 27
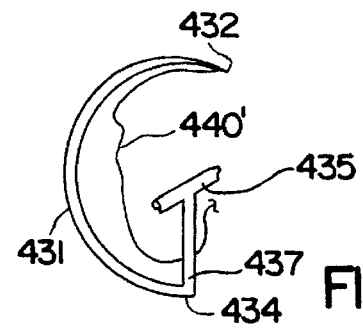
FIG. 28
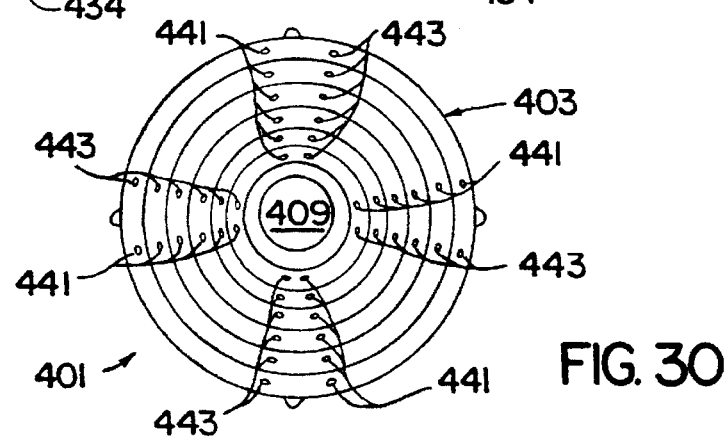
FIG. 30

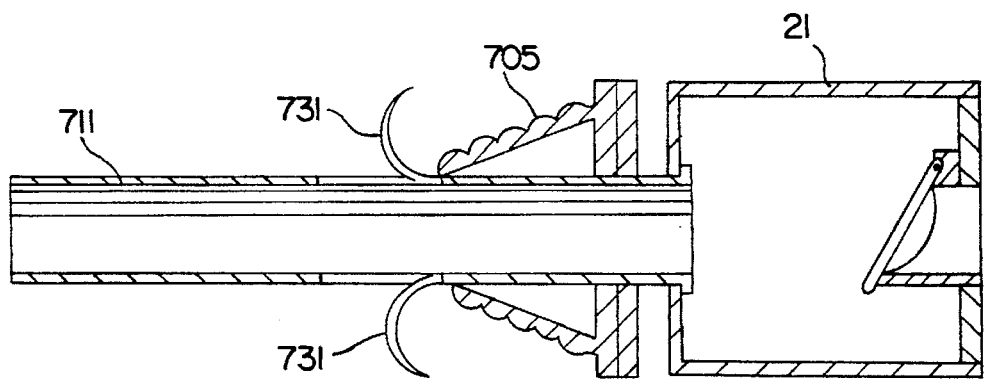
FIG. 45
FIG. 47
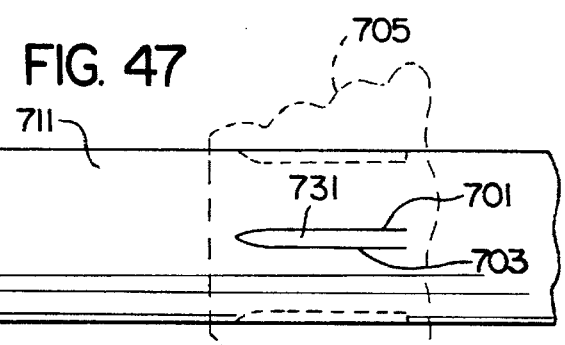
FIG. 46
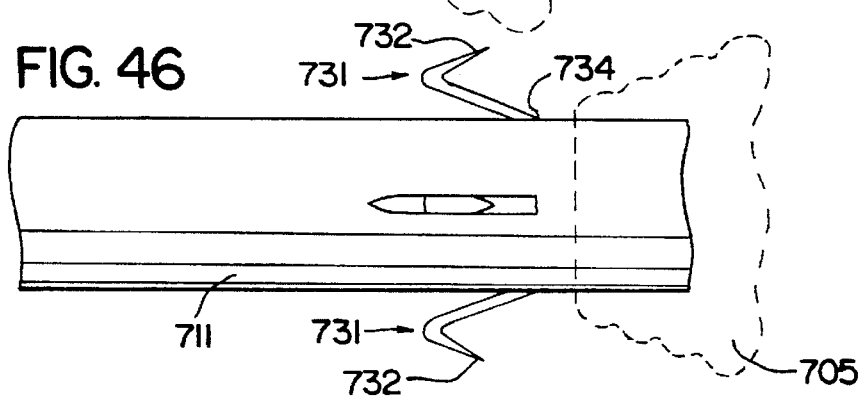

CANNULA ANCHORING SYSTEM

BACKGROUND OF THE INVENTION

1. Field of the Invention

The present invention pertains to medical procedures and instruments and, more particularly, to a system for anchoring a cannula in an anatomical cavity wall.

2. Discussion of the Prior Art

Endoscopic and minimally invasive medical procedures are widely used for surgical and diagnostic treatment and viewing in an anatomical cavity and generally utilize a cannula, such as portal sleeve, inserted through a wall of the anatomical cavity to provide a passage for introduction of instruments into the cavity. In many endoscopic procedures, access to the anatomical cavity is gained by utilizing a penetrating instrument composed of a penetrating member, such as a trocar or obturator, within a portal sleeve to penetrate the wall of the cavity with the penetrating member thereafter withdrawn leaving the portal sleeve in place to establish a portal for introducing instruments into the anatomical cavity. The portal sleeve typically has a proximal end disposed externally of the anatomical cavity and coupled with a portal housing mounting a valve and sealing arrangements allowing the penetrating member and other instruments to be inserted into and removed from the sleeve while preventing leakage of fluids from the anatomical cavity. The portal sleeves are subject to longitudinal and angular movement during the procedures due to the movement of instruments therethrough and the manipulation of the instruments within the cavity particularly since the instruments are sealingly engaged along the portal sleeve particularly at the housing. It has, thus, become important to securely anchor the portal sleeve to the cavity wall and to stabilize the portal sleeve in a desired angular orientation relative to the cavity.

Many anchoring and/or stabilizing devices are available and, typically, utilize arrangements such as expandable devices in the form of inflatable balloons, mechanically hinged legs or mechanically or pneumatically expandable members for contacting, in an expanded state, an internal surface of the cavity wall and/or members for contacting and/or sealing an external surface of the cavity wall as exemplified by U.S. Pat. No. 3,039,648 to Price, U.S. Pat. No. 3,253,594 to Matthews et al, U.S. Pat. No. 3,817,251 to Hasson, U.S. Pat. No. 3,952,742 to Taylor, U.S. Pat. No. 5,002,557 to Hasson, U.S. Pat. No. 5,073,169 to Raiken, U.S. Pat. No. 5,122,122 to Allgood, U.S. Pat. No. 5,137,520 to Maxson et al, U.S. Pat. No. 5,147,316 to Castillenti, U.S. Pat. No. 5,176,648 to Holmes et al, U.S. Pat. No. 5,176,697 to Hasson et al, U.S. Pat. No. 5,203,773 to Green, U.S. Pat. No. 5,215,531 to Maxson et al, U.S. Pat. No. 5,217,451 to Freitas, U.S. Pat. No. 5,232,451 to Freitas et al, U.S. Pat. No. 5,234,455 to Mulhollan, U.S. Pat. No. 5,263,939 to Wortrich, U.S. Pat. No. 5,267,970 to Chin et al, U.S. Pat. No. 5,273,545 to Hunt et al, U.S. Pat. No. 5,257,975 to Foshee, U.S. Pat. No. 5,279,564 to Taylor, U.S. Pat. No. 5,279,575 to Sugarbaker, U.S. Pat. No. 5,284,474 to Adair and U.S. Pat. No. 5,290,249 to Foster et al. Additionally, spiral threads or other protrusions carried by a cannula for engaging a cavity wall along the thickness thereof have been proposed as exemplified by U.S. Pat. No. 4,655,752 to Honkanen et al, U.S. Pat. No. 5,009,643 to Reich et al, U.S. Pat. No. 5,217,441 to Schichman, U.S. Pat. No. 5,226,890 to Ianniruberto et al, U.S. Pat. No. 5,248,298 to Bedi et al, U.S. Pat. No. 5,258,003 to Ciaglia et al, U.S. Pat. No. 5,271,380 to Rick et al and U.S. Pat. No. 5,273,545 to Hunt et al, and the Endopath Adjustable Stability Threads sold by Ethicon Endo-Surgery. Other anchoring and/or stabilizing devices, such as those described in U.S. Pat. No. 5,257,973 to Villasuso, have attempted to maintain the position of the portal sleeve during the procedure by attaching hooks or clamps to the cannula and using a length of suture material to tie the hooks or clamps to a patient's body tissue. U.S. Pat. No. 4,985,033 to Boebal et al is representative of devices for sealing openings used in open laparoscopy and for fixing fascial holding sutures.

Additionally, in other medical procedures, it is important to securely anchor cannulas, such as catheters, in place in anatomical cavity walls to provide a portal for access to the cavity to allow passage for instruments and/or fluids. The anchoring must be accomplished in as safe and non-traumatic manner as possible, and anchoring in a cavity wall such as that of an internal organ must be precisely accomplished in a simple manner to facilitate use and permit readjustment at surgical sites which are easily accessible or are difficult to access, such as in endoscopic or minimally invasive procedures.

The use of tissue penetrating members has been suggested for use in devices to hold needles and catheters in place on a patient, as exemplified by U.S. Pat. No. 2,670,735 to Brody and U.S. Pat. No. 4,164,943 to Hill et al; however, such devices cannot be used to anchor cannulas passing substantially transversely through a cavity wall and the devices.

The above discussed anchoring and/or stabilizing devices have the disadvantages of being difficult to use in securely angularly orienting cannulas and reorienting the cannulas during a procedure, of not adequately grasping an anatomical cavity wall to permit manipulation or lifting of the wall due to all of the lifting or manipulating force being applied to the internal surface of the wall, e. g. the peritoneum in the case of laparoscopy, of frequently requiring resetting or reanchoring and/or of being time consuming and difficult to use.

SUMMARY OF THE INVENTION

Accordingly, it is a primary object of the present invention to overcome the above mentioned disadvantages of the prior art by anchoring a cannula in an anatomical cavity wall with the use of one or more tissue penetrating members carried by the cannula.

Another object of the present invention is to anchor a cannula in an anatomical cavity wall in a manner to prevent longitudinal movement of the cannula and to facilitate stabilizing of the cannula in a desired angular orientation relative to the cavity wall and the cavity.

A further object of the present invention is to penetrate a cavity wall with a needle carried by a cannula to permit lifting or manipulation of the cavity wall with or without engagement of the internal surface of the cavity wall.

An additional object of the present invention is to anchor a cannula within the thickness of a cavity wall by deploying at least one tissue penetrating member to protrude into the thickness of the cavity wall.

The present invention has another object in that tissue penetrating members are used to anchor and/or stabilize a cannula in a cavity wall and further to pass suture material through the constituent layers of the cavity wall, such as, in the case of the abdomen, the peritoneum, muscle, fascia, fat and/or skin, whereby the puncture site in the cavity wall can be closed by drawing the suture material together after the cannula has been withdrawn.

Another object of the present invention is to utilize tissue penetrating members to form one or more closed spaces to capture tissue to securely anchor a cannula within a wall of an anatomical cavity.

An additional object of the present invention is to utilize hollow needles as tissue penetrating members in a cannula anchoring system to permit injection of medicaments through the needles.

A further object of the present invention is to arrange tissue penetrating members on a device carried by a cannula such that the cannula passes through the device and can be anchored in a cavity wall by the tissue penetrating members.

Some of the advantages of the present invention over the prior art are that secure anchoring is achieved with tissue penetrating members while permitting the cannula to be handled with the tissue penetrating members in a protected, non-exposed position, the tissue penetrating members can be disposed at various locations and angular orientations to facilitate anchoring and/or stabilization for numerous endoscopic and minimally invasive procedures, cavity walls can be manipulated or lifted to provide increased exposure and facilitate comfortable endoscopic diagnostic and surgical procedures, hollow tissue penetrating members can be used to permit medicaments, such as anesthetic agents, to be administered to the surrounding tissue therethrough, the tissue penetrating members can be used to facilitate puncture site closure and to pull tissue against the cannula to prevent leakage of fluids from the cavity and the anchoring system is designed to facilitate use in a simple, quick and efficient manner.

The present invention is generally characterized in a cannula anchoring system for stabilization, manipulation and/or puncture site closure wherein at least one tissue penetrating member is carried by the cannula at a position adjacent a wall of an anatomical cavity when the cannula is inserted through the cavity wall and is movable between a non-exposed, retracted position and an exposed, extending position protruding from the cannula and an operating mechanism is coupled with the tissue penetrating member to move the tissue penetrating member between the retracted and extended positions. The tissue penetrating members can be carried or supported by the cannula in any manner whereby insertion of the tissue penetrating members in the cavity wall serves to anchor the cannula, for example, by the tissue penetrating members being mounted on a housing immovably secured to the cannula, such as a valve housing at the proximal end of a portal sleeve, by the tissue penetrating members being mounted on a housing movable along the cannula, such as a stabilizer movable along a portal sleeve, or by the tissue penetrating member being mounted directly on the cannula.

The present invention is further generally characterized in a method of performing a medical procedure in an anatomical cavity including the steps of inserting a cannula through a wall of the anatomical cavity, penetrating the cavity wall adjacent the cannula with at least one needle carried by the cannula to anchor the cannula to the cavity wall, withdrawing the needle from the cavity wall, and removing the cannula. The method allows the cannula to be adjusted to achieve a desired angular orientation relative to the anatomical cavity with the use of a plurality of needles, allows lifting or manipulating the cavity wall by grasping and moving the cannula away from the cavity due to the cannula being anchored to the cavity wall by the needles and allows closing of the puncture site to be accomplished by penetrating tissue along the thickness of the cavity wall at the puncture site with the needles, using the needles to pass lengths of suture material through the tissue along the thickness of the cavity wall at the puncture site and, after the cannula is removed, drawing the lengths of suture material together to suture the puncture site closed.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 25 is a side view, partly in section, showing a further modification of a cannula anchoring system according to the present invention facilitating puncture site closure.

FIG. 26 is a perspective view of the needle assembly of the anchoring system of FIG. 25.

FIG. 27 is a broken view of a hollow anchoring needle for use with the anchoring system of FIG. 25 to permit passage of a length of suture material therethrough.

FIG. 28 is a broken view of an anchoring needle for use with the anchoring system of FIG. 25 with a length of suture material attached to the distal end thereof.

FIG. 29 is a section taken along line 29—29 in FIG. 25.

FIG. 30 is a distal end view of the anchoring system of FIG. 25.

FIG. 45 is a sectional view of a cannula anchoring system according to the present invention wherein anchoring needles are formed integrally with a portal sleeve.

FIGS. 46–49 are views showing use of the anchoring system of FIG. 45.

DESCRIPTION OF THE PREFERRED EMBODIMENTS

The anchoring system of the present invention can be utilized to anchor any type of cannula in a cavity wall to provide access to any type of anatomical cavity; and, accordingly, while the anchoring system is described hereinafter for use with a portal sleeve for use in endoscopic procedures, such as laparoscopy, the anchoring system can be used to anchor catheters and other small and large diameter cylindrical members to provide access to small cavities as well as large cavities, such as the abdomen. The anchoring system of the present invention is carried by a cannula in a manner such that deployment of needles to penetrate tissue of a cavity wall anchors the cannula to the cavity wall; and by "carried" the present invention contemplates the mounting of the tissue penetrating needles on any structure associated with a cannula in a manner whereby penetration of needles into the cavity wall anchors the cannula to the cavity wall. While the structure described hereinafter relates to a portal sleeve, where the anchoring system is used with other types of cannulas, the needles can be carried by structures having configurations and sizes corresponding to the specific cannulas. For example, the needles can be carried on housings or hubs secured along the cannulas or on the proximal ends of the cannulas or on housings movable along the cannulas or integrally formed with or mounted directly on the cannulas.

Figure 1:
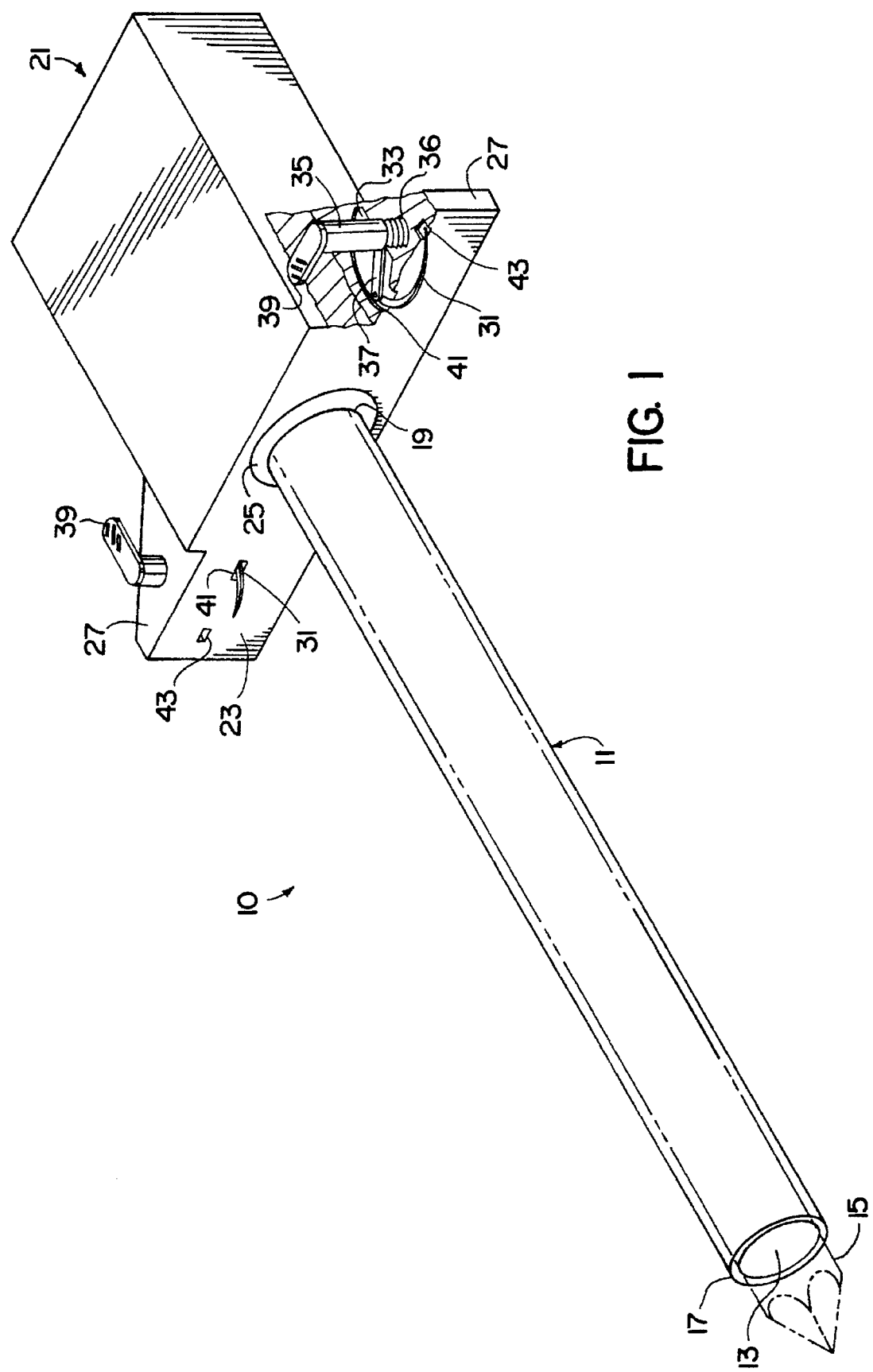
FIG. 1 is a perspective view, partly in section, of a cannula anchoring system according to the present invention.
Figure 2:
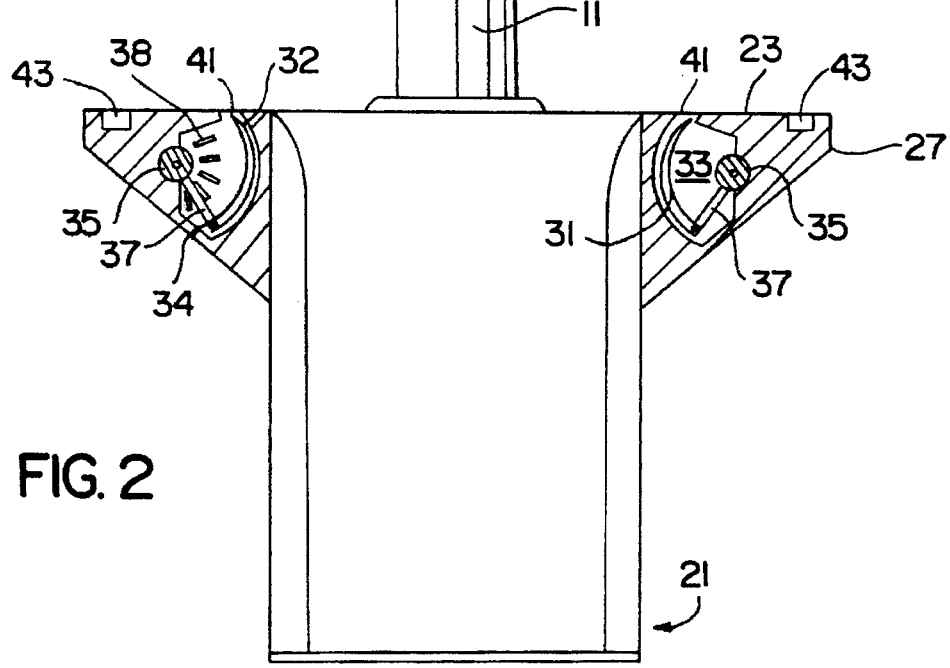
FIG. 2 is a top view, partly in section, of the cannula anchoring system of FIG. 1.

A cannula anchoring system 10 according to the present invention is illustrated in FIGS. 1 and 2, for use with an elongate tubular or cylindrical portal sleeve 11 having a lumen 13 receiving an obturator or penetrating member 15, such as a trocar, to provide access to an operative site within an anatomical cavity. Portal sleeve 11 has a distal end 17 for being disposed within the anatomical cavity and a proximal end 19 for being disposed externally of the cavity with the sleeve 11 inserted through the cavity wall. A housing 21 receives the proximal end 19 of portal sleeve 11 in an opening in a front wall 23 of the housing defined by a frusto-conical nipple or ring 25.

Housing 21 can have any desirable configuration to house a valve controlling flow through the housing 21 and portal sleeve 11 and has opposed flared wings 27 extending from front wall 23. The portal sleeve 11, housing 21 and penetrating member 15, as thus far described, form a conventional penetrating instrument for use in endoscopic procedures and can have any desired configurations and be made of any desired materials in order to be disposable for single patient use or sterilizable for reuse.

Figure 3:
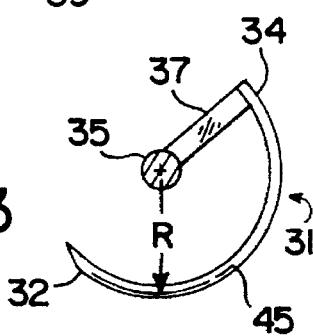
FIG. 3 is an enlarged top view, partly in section, of an anchoring needle according to the present invention.

In accordance with the present invention, one or more tissue penetrating members, such as anchoring needles 31, are movably disposed within pockets or cavities 33 defined within the flared wings 27 of housing 21. As best seen in FIG. 3, each needle 31 includes an arcuate and preferably semi-circular body of circular cross-section having a distal end 32 terminating in a sharp tip and a proximal end 34 connected along an inner peripheral edge thereof to an inwardly extending radial arm 37. The radial arm 37 is coplanar with needle 31 and is connected to a perpendicularly extending shaft 35 rotatably supported in housing 21. A radially extending handle 39 is secured to each rotatable shaft 35 externally of housing 21.

The radius of curvature of the needle 31 and position of the rotatable shaft 35 within housing 21 are chosen to provide a suitable amount of needle protrusion from the front wall 23 of the housing 21 to securely fasten the housing 21 to the wall of an anatomical cavity. Hence, the radius of curvature and configuration of the needles 31 will vary depending on the thickness and consistency of the anatomical cavity being accessed. For example, with a radius of curvature R of about 18 mm, a typical amount of protrusion would be from about 8 mm to about 12 mm, depending on where the rotatable shaft 35 is arranged relative to the front wall 23 of the housing 21.

Pockets 33 extend proximally into the flared wings 27 of housing 21 from openings 41 in the front wall 23 and form recesses configured to receive needles 31 and to provide clearance for rotation of the radial arm 37. In a non-exposed, retracted position, shown in FIG. 2, needles 31 are disposed completely within pockets 33 with sharp distal ends thereof safely maintained behind openings 41 in the front wall 23. The needles 31 are moveable between the retracted position and an exposed, extending position wherein the sharp distal ends 32 of needles 31 protrude distally from openings 41. In FIG. 1, for example, the needle on the right is shown in a fully extended position wherein the needle protrudes distally from opening 41 and loops back into front wall 23. The sharp distal end 32 of the fully extended needle 31 is received in a recess 43 defined in the front wall 23 and laterally spaced from opening 41. For purposes of illustration, the needle on the left in FIG. 1 is shown extended only part way, leaving the sharp distal end 32 exposed.

Figure 4:
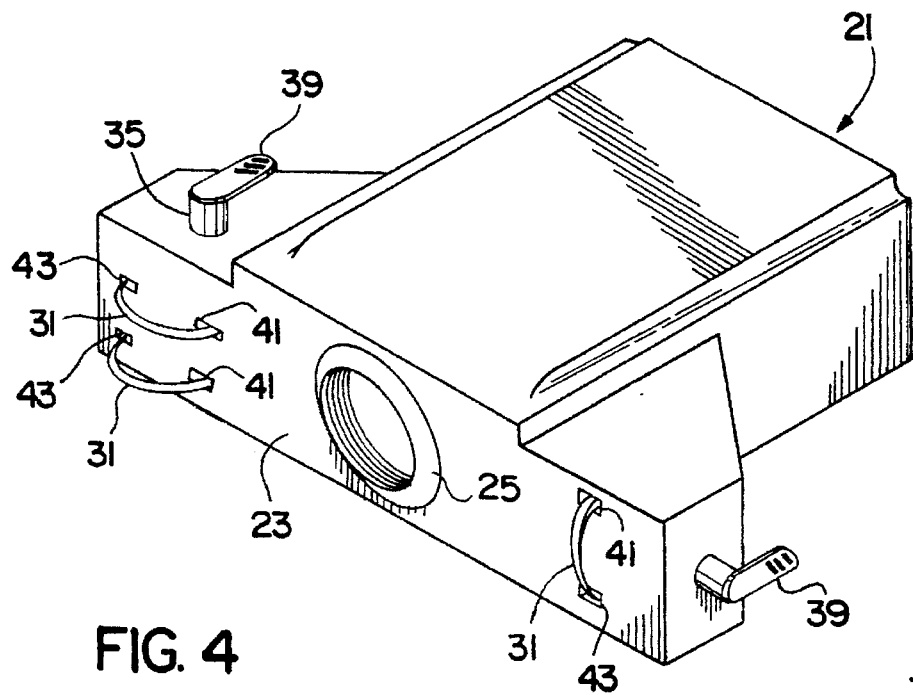
FIG. 4 is a perspective view of a portal housing according to the present invention in which needles rotate in planes perpendicular to one another and plural needles are provided on a flared wing of the housing.
Figure 5:
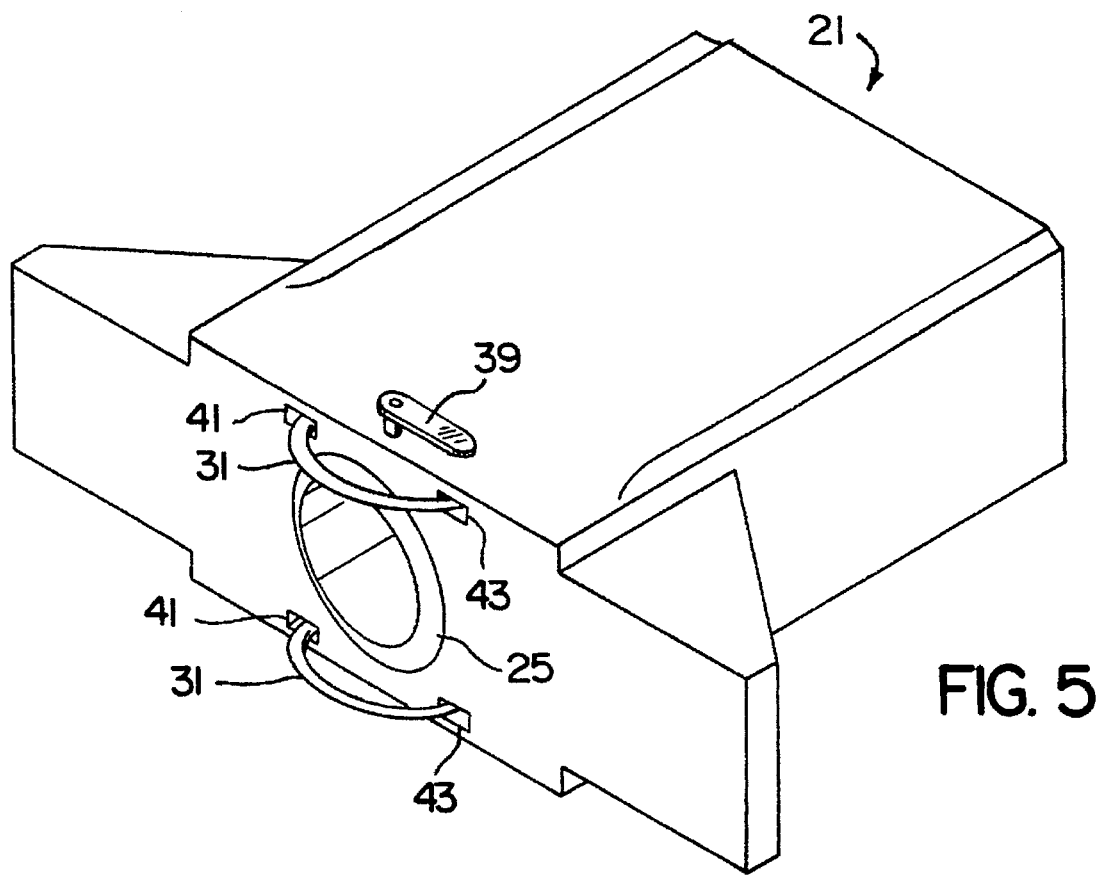
FIG. 5 is a perspective view of a portal housing according to the present invention in which needles rotate in parallel planes above and below a cannula.

Needles 31 are deployable from flared wings 27 of the portal housing 21 to maximize the lateral spacing between the needles and thus the lateral stability of the portal sleeve. In FIG. 1, needles 31 are rotatable in a single plane including the longitudinal axis of the portal sleeve; however, the needles can also be positioned to rotate in a single plane displaced from the longitudinal axis of the portal sleeve or in perpendicular planes as shown in FIG. 4, in spaced parallel planes above and below the portal sleeve 11 as shown in FIG. 5, or at any other location on housing 21 and in any other direction relative to one another dependent upon particular anatomical cavities being accessed, procedures being performed and the angular orientation required. Plural needles may also be provided at any anchoring location on housing 21, alone or in combination with plural or single needles at other anchoring locations, as demonstrated in FIG. 4, and can be simultaneously rotatable about a single shaft by common connection thereto or individually rotatable. It will also be appreciated that any of the foregoing needle arrangements can be employed alone or in combination to achieve a desired stability and ease of use.

It is preferred that the needles 31 be lockable in retracted and deployed positions, respectively, or any position therebetween. To this end, each rotatable shaft 35 engages a tension spring 36 which biases the shaft 35 toward a plurality of ridges or protrusions 38 formed on a bottom wall of the pocket 33 and radially spaced around shaft 35 as shown in FIG. 2 to normally hold radial arm 37 therebetween.

Figure 6:
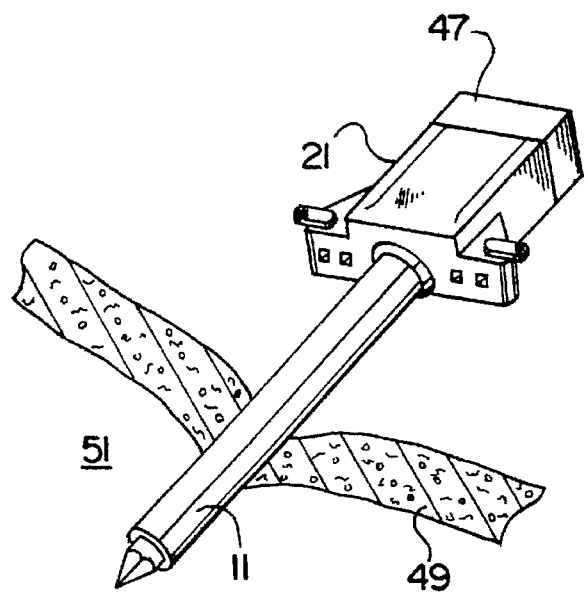
Figure 7:
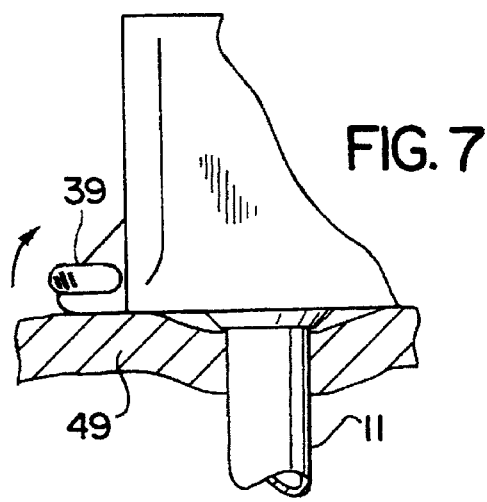
Figure 8:
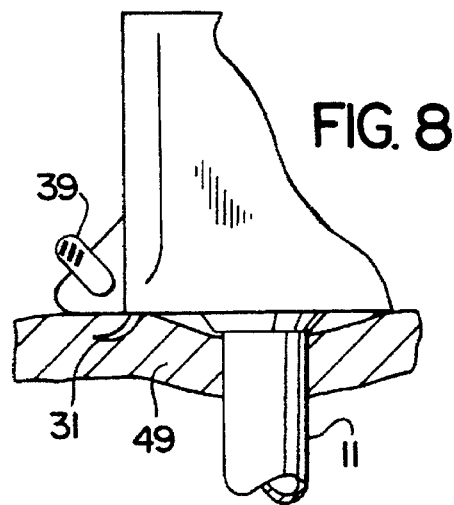
Figure 9:
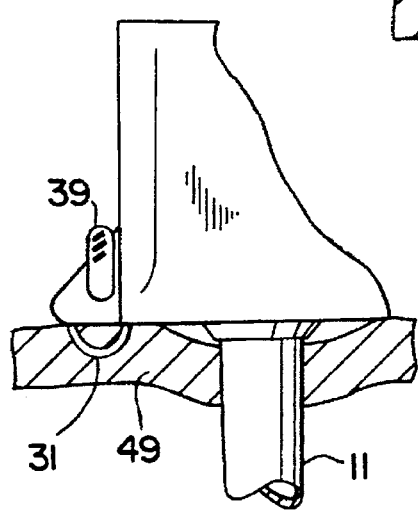

In use, the penetrating member 15 is slidably disposed within the portal sleeve 11 with a hub 47 at the proximal end of the penetrating member abutting housing 21, as shown in FIG. 6. With the sharp distal ends of needles 31 retracted into cavities 33, the housing 21 and hub 47 are grasped by positioning two fingers around the portal sleeve 11 against front wall 23 without touching the needles. The penetrating member 15 is then used to puncture a wall 49 of an anatomical cavity 51 so that the portal sleeve 11 is introduced into the cavity 51. After insertion of the portal sleeve 11, the penetrating member 15 is withdrawn from the sleeve 11, and the sleeve 11 urged into the cavity 51 until the front wall 23 of the portal housing 21 nears an external surface of the cavity wall 49 as shown in FIG. 7. Once the housing 21 is adjacent the cavity wall 49, the anchoring needles 31 are moved from their retracted positions by lifting handles 39 away from the housing 21 against the bias of springs 36 to elevate radial arms 37 above protrusions 38 and by turning each handle 39 away from a position parallel to front wall 23 to cause the needles to penetrate into the tissue of the cavity wall as shown in FIG. 8. During penetration, the sharp distal end 32 of each needle 31 is displaced through the opening 41 formed in the front wall 23 of the housing 21 and into the anatomical cavity wall 49. Rotation of each handle 39 is continued until perpendicular to front wall 23 or until the needles 31 protrude from the front wall 23 of housing 21 as shown in FIG. 9 to capture tissue between the arcuate body 45 of each needle 31 and the front wall 23 of the housing 21 thereby anchoring the portal sleeve 11 in place. Since rotation of handle 39 outside housing 21 causes concomitant rotation of rotatable shaft 35, radial arm 37 and arcuate needle 31, the position of each needle 31 within the cavity wall 49 can be determined by the position of handles 39. When the needles 31 are extended to a desired extent, handles 39 are released to lock needles 31 in the extended position by allowing tension spring 36 to draw the shaft 35 downward thereby capturing radial arm 37 between the pairs of protrusions 38. When fully extended, the distal end 32 of the needles will be received in recesses 43 to form a closed space capturing tissue of the cavity wall therein; however, the needles can be positioned anywhere between retraction and full extension and locked in similar fashion.

Figure 10:
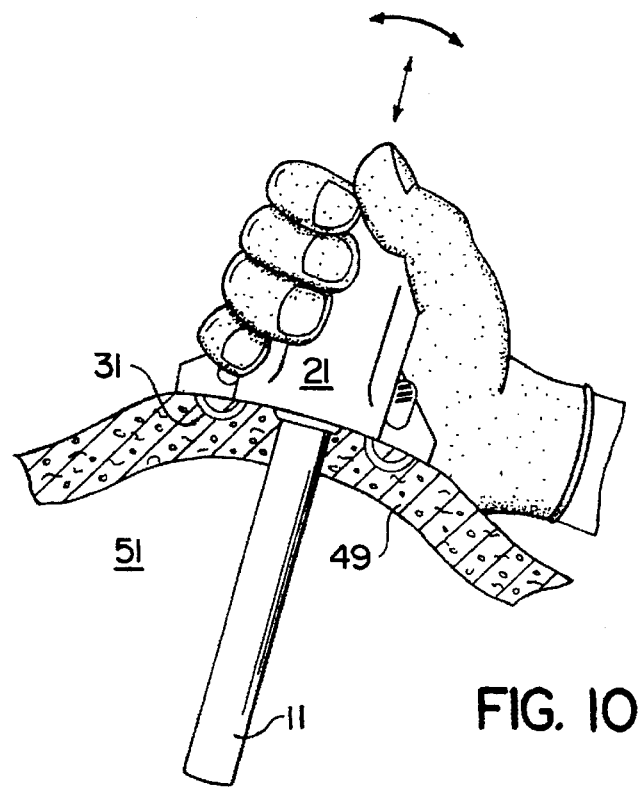

With the needles penetrating into the cavity wall, the cannula anchoring system of the present invention permits manipulation or lifting of the wall of the anatomical cavity to improve exposure, for example, as well as anchoring the portal sleeve to the cavity wall at a desired angular orientation. As illustrated in FIG. 10, movement of the cavity wall is accomplished easily by grasping the housing 21 and urging it in the desired direction.

Figure 11:
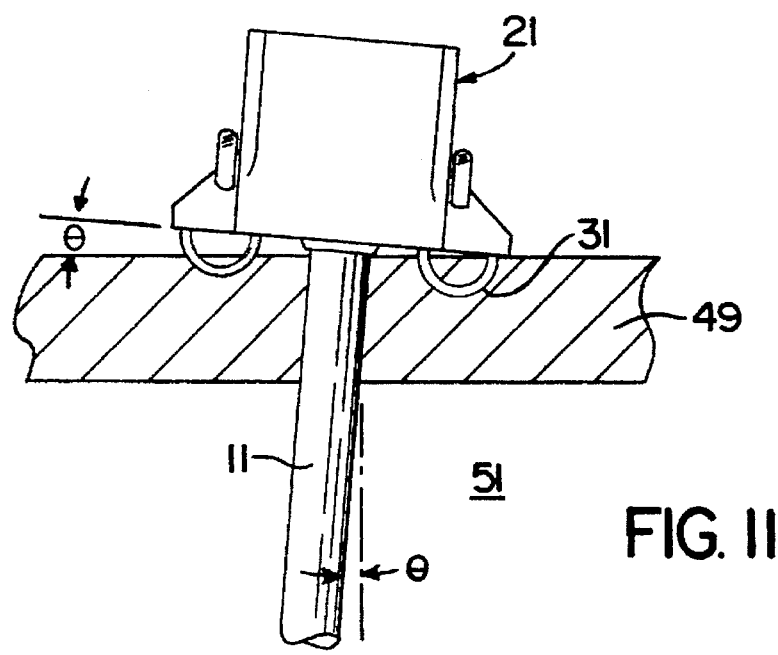
FIGS. 6–11 are broken views, partly in section, illustrating use of the anchoring system of the present invention.

The anchoring system of the present invention can be used to stabilize portal sleeve 11 in a desired angular orientation relative to cavity wall 49 by orienting the housing 21 relative to cavity wall 49 with needles 31 retracted and then deploying needles 31 from their respective pockets within housing 21 into the extended positions to pierce the cavity wall 49. Since the front wall 23 of housing 21 is tilted relative to cavity wall 49, needles 31 will achieve various depths of penetration as shown in FIG. 11 to set and hold the portal sleeve 11 in the desired angular orientation relative to the cavity wall 49.

Removal or repositioning of the portal sleeve 11 is easily accomplished by lifting each handle 39 away from the housing 21 to elevate radial arm 37 above the protrusions 38 and rotating the handle 39 from the position perpendicular to the front wall 23 of the housing 21 to the position parallel to the front wall 23, thereby withdrawing each needle 31 into its retracted position within the housing 21. With needles 31 retracted, sharp distal ends 32 are no longer exposed, allowing the portal housing 21 to be grasped in the vicinity of front wall 23 for removal or repositioning.

Figure 12:
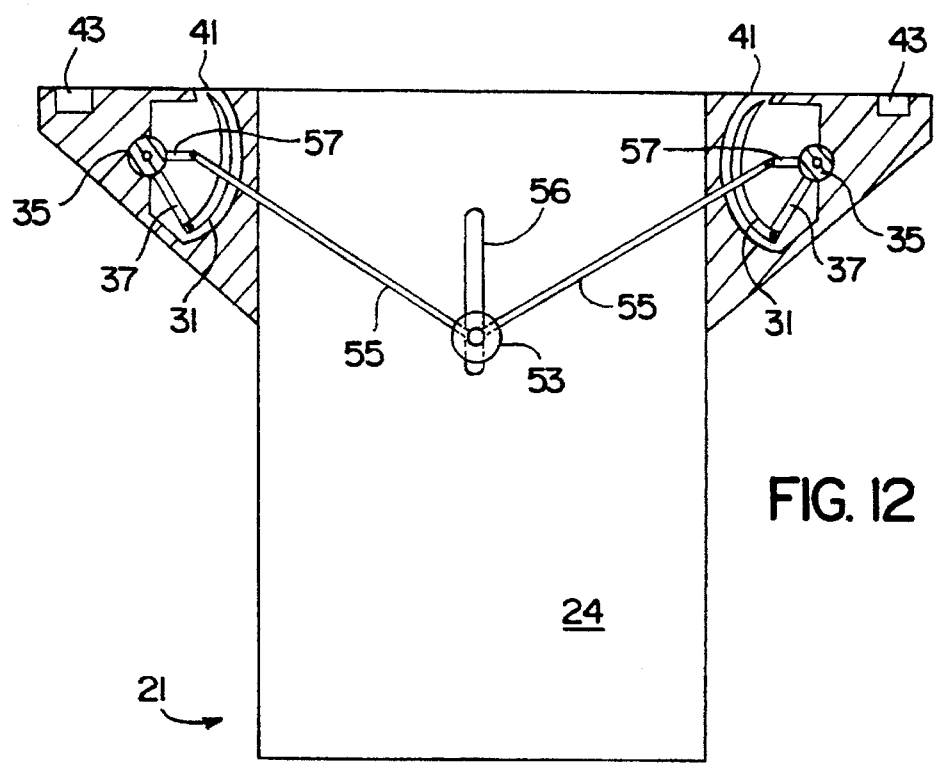
FIG. 12 is a top view, partly in section, of a cannula anchoring system of the present invention modified for simultaneous deployment of the anchoring needles.

A modification of the cannula anchoring system 10 of the present invention is shown in FIG. 12 with the primary difference being the provision of a single actuating mechanism for deploying multiple anchoring needles simultaneously. The structure of the portal housing 21, needles 31, cavities 33 and radial arms 37, which connect the needles 31 to respective perpendicularly extending shafts 35, are essentially the same as previously described, with the exception that shaft 35 need not extend externally of portal housing 21. Additionally, a single handle or tab 43 is located externally of a top wall 24 of the portal housing 21 and includes a downwardly extending leg extending through a longitudinally extending slot 56 defined in the top wall 24 of the housing 21 to be pivotally coupled with one or more pairs of pivoted arms 55 and 57. Each pair of pivoted arms 55 and 57 forms a linkage between handle 53 and a respective rotatable shaft 35 to cause rotation thereof.

Use of the anchoring system of FIG. 12 differs primarily in the method of deploying the needles 31. Penetration of the cavity wall and placement of the portal sleeve proceed essentially in the same manner; however, with front wall 23 of the portal housing 21 adjacent the cavity wall, deployment of needles 31 from the retracted position into the tissue of the cavity wall is accomplished by linear translation of the handle 53 distally in elongate slot 56. Distal movement of handle 53 causes pivot arms 55 to thrust laterally outward against pivot arms 57. Since pivot arms 57 are secured to rotating shaft 35, they rotate as a consequence of the outward thrust and thus cause a pivoting of each rotatable shaft 35 and concomitant rotation of needles 31 from the retracted position within pockets 33 to extended positions forward of front wall 23. Locking of the needles in either or both of the retracted and fully deployed positions, or any position therebetween, can be accomplished in the manner previously described by supporting handle 53 on a spring so that it is downwardly biased and providing a plurality of recesses within the housing 21 to normally retain the downwardly extending protrusion of handle 53.

Figure 13:
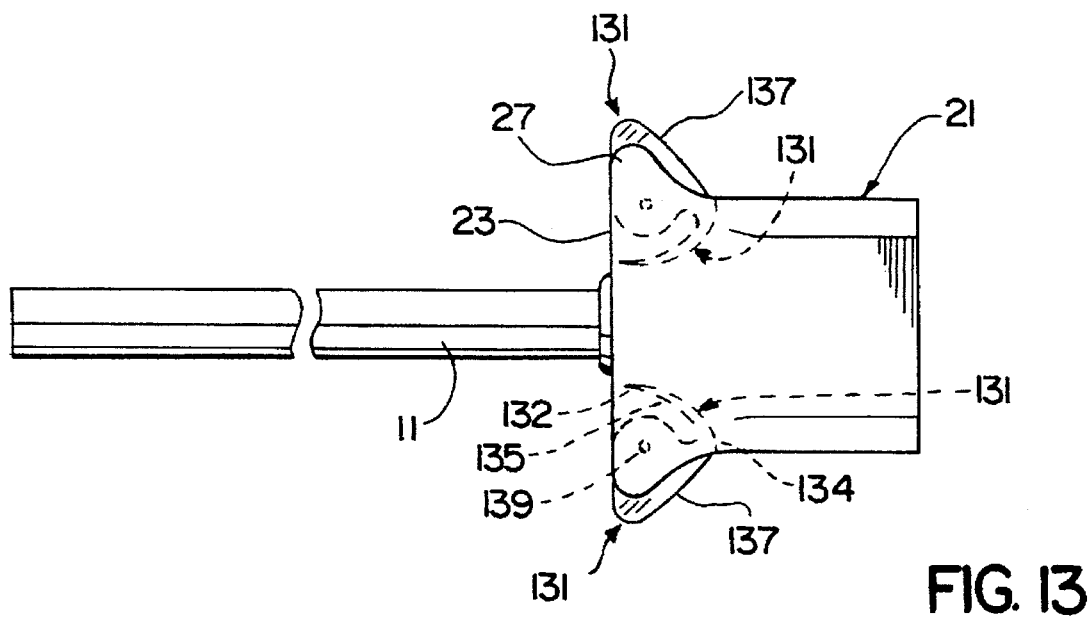
FIG. 13 is a top view of a cannula anchoring system of the present invention utilizing needles with integral handles.
Figure 14:
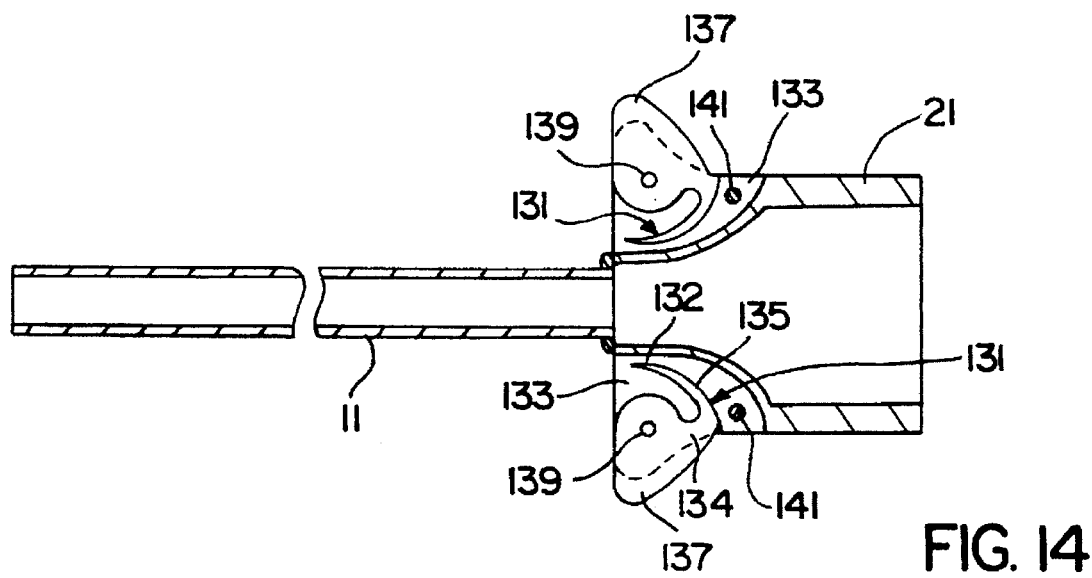
FIG. 14 is a top view, partly in section, showing the cannula anchoring system of FIG. 13 with the needles in a non-exposed, retracted position within the portal housing.
Figure 15:
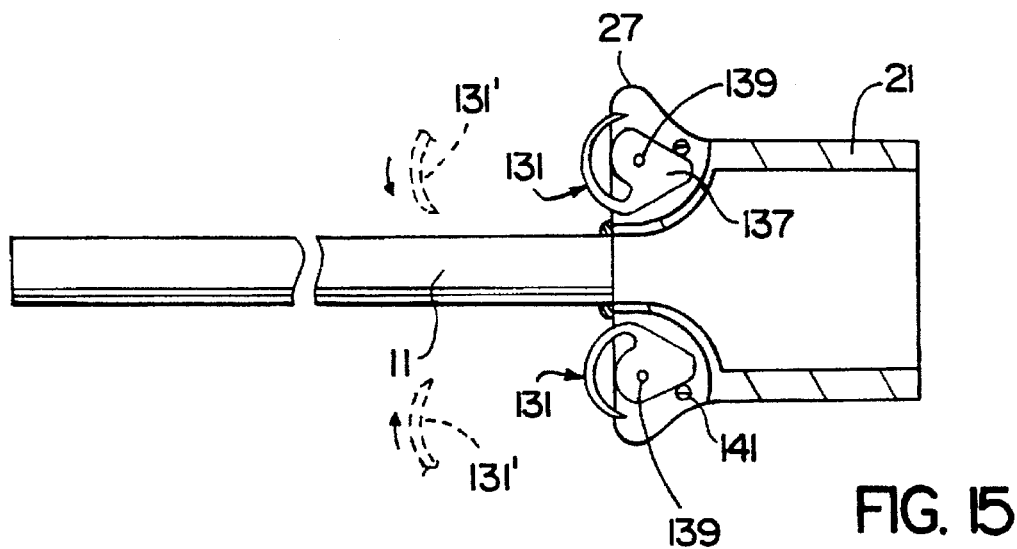
FIG. 15 is a top view, partly in section, showing the cannula anchoring system of FIG. 13 with needles in an exposed, extending position.
Figure 16:
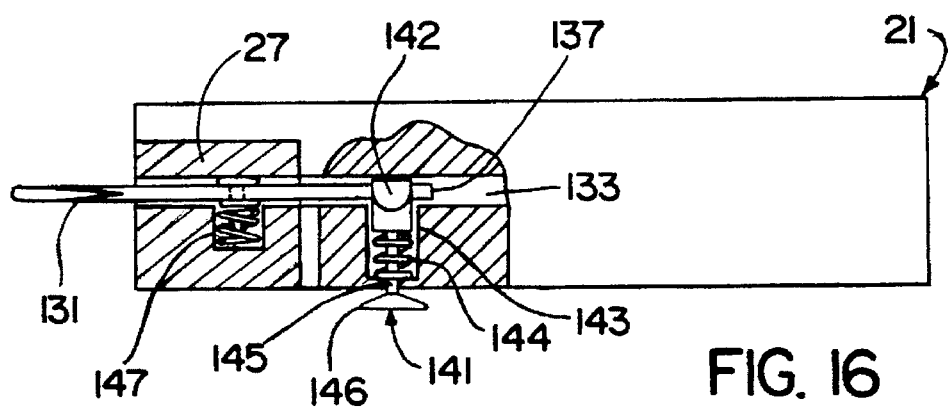
FIG. 16 is a side view, partly in section, of the cannula anchoring system of FIG. 13 showing a manually releasable locking detent.

Another modification of the anchoring system of the present invention is shown in FIGS. 13–17, with the primary difference being the construction of anchoring needles 131 which include a sharp tip at a distal end 132 thereof, a proximal end 134 terminating at an integral handle 137 and an arcuate needle body 135 disposed intermediate the proximal and distal ends 132 and 134. Each needle 131 is preferably formed as a unitary piece and can be made of any suitable material, such as stainless steel. The needles 131 are movably disposed within slot-like pockets 133 defined primarily in flared wings 27 and are pivotally mounted on pins 139 within the pockets 133. Integral handles 137 are dimensioned and shaped to extend laterally outward from the flared wings 27 of the portal housing 21 with the needles 131 retracted as shown in FIGS. 13 and 14. Locking detents 141 extend perpendicularly into needle pockets 133 and are spaced proximally of needles 131 to engage integral handles 137 as shown in FIG. 15 when the handles 137 are rotated into pockets 133. As best seen in FIG. 16, locking detents 141 each includes a piston 142 slidably disposed within a recess 143 defined in a bottom wall of needle pocket 133. Each piston 142 includes a chamfered top surface and a bottom engaging a spring 144 mounted in compression within recess 143. A piston rod 145 extends through the spring 144 and is connected between the bottom end of piston 142 and a handle 146 externally of housing 21. When handle 146 is pulled away from housing 21, piston rod 145 draws piston 142 downward within recess 143 against the force of spring 144. With needles 131 biased toward the retracted positions using torsion springs 147, pulling of handle 146 will automatically retract the needles 131. In a similar fashion, the needles 131 can be biased by torsion springs to automatically extend and penetrate into the cavity wall; and, by use of an additional spaced detent, both automatic deployment and retraction can be accomplished.

With front wall 23 of the housing 21 adjacent the cavity wall, deployment of needles 131 from the retracted position into the tissue of the cavity wall is accomplished by drawing back handles 137 into the pockets 133. Integral handles 137 bear against the chamfered surface of detents 141 to compress compression springs 144, allowing passage of the handles 137 over the detents 141. When a trailing edge of handle 137 passes over detent 141, spring 144 urges the detent 141 upward to bear against and obstruct the trailing edge of the integral handle 137. The needles 131 are thus locked in an exposed, extending position. The needles 131 are unlocked by pulling the externally located handle 146 away from housing 21, thereby causing piston 142 to recede into recess 143 and allowing needle 131 to rotate from the extended position to the retracted position under the influence of the torsional bias created by spring 147.

Figure 17:
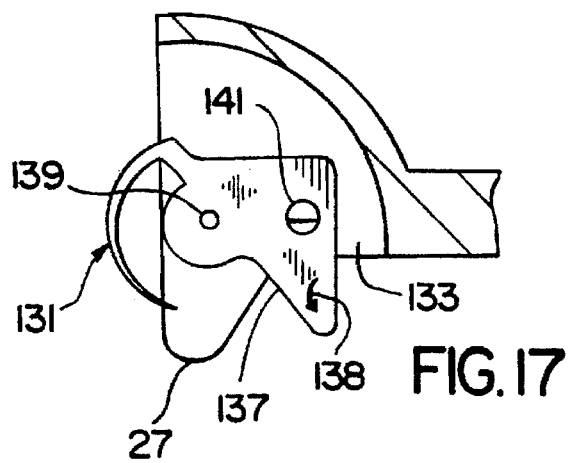
FIG. 17 is a broken section showing an alternative needle and handle configuration with the needle in an exposed, extending position.

In FIG. 17, an alternative handle profile is shown in which a portion of the handle 137 protrudes externally of the portal housing 21 in the extended position to further facilitate manual manipulation of the handle 137 and carries indicia such as an arrow 138 indicating the position of the needle.

Figure 18:
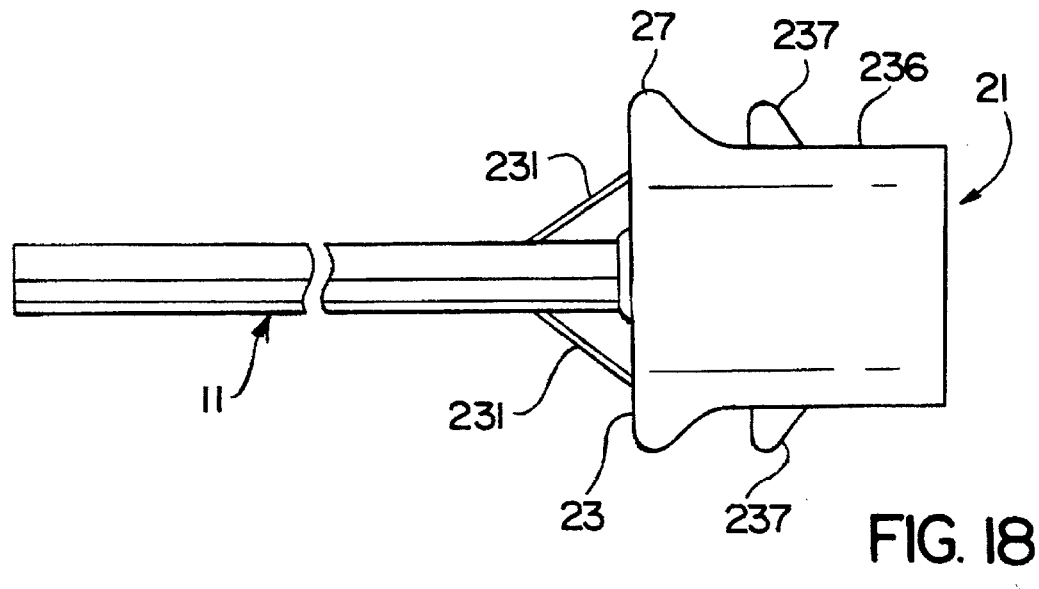
FIG. 18 is a top view of another modification of the cannula anchoring system of the present invention using straight needles.
Figure 19:
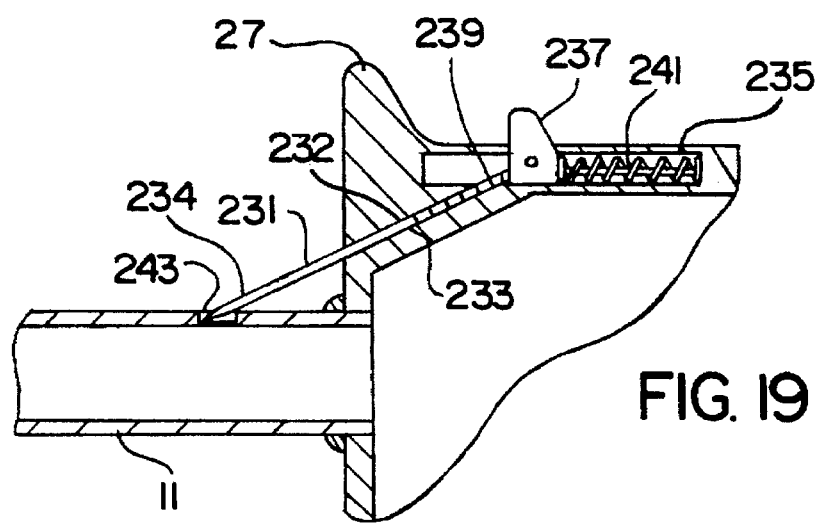
FIG. 19 is a broken section of the cannula anchoring system of FIG. 18.

The anchoring system illustrated in FIGS. 18 and 19 employs straight needles 231 and is particularly useful with rigid cavity walls. Handles 237 are coupled with proximal ends of the needles and are translatably disposed in elongate slots 235 defined in side walls 236 of the housing 21. A flexible coupling 239 is attached between each handle 237 and the proximal end 232 of straight needle 231 which is slidably disposed within a tubular needle pocket 233. Needles 231 each have a sharp tip at a distal end 234 thereof and are obliquely supported within the cavities 233 relative to the front wall 23 of the housing 21 and the longitudinal axis of the portal sleeve 11. A spring loaded catch or detent 241 is incorporated into each slot 235 to normally urge the handle 237 in a proximal direction and to lock the handle 237 in predetermined proximal and distal positions, or at any other position within slot 235. Recesses 243 are disposed in the portal sleeve 11 and aligned to receive the sharpened tips of needles 231 when deployed to form closed loops for capturing tissue therein. If the portal sleeve 11 is constructed of a soft material, the tip of each needle 231 can lodge in the portal sleeve 11 without requiring a separate recess 243.

In use, distal translation of the handle 237 in the slot 235 causes needle 231 to translate distally from a retracted position within pocket 233 toward an opening in front wall 23. The sharp tip of needle 231 emerges obliquely from the opening in the front wall 23 to pierce the tissue of the cavity wall. In an exposed, extending position, the needle 231 protrudes from the front wall 23 of the portal housing 21 into the portal sleeve 11 at an oblique angle to both the front wall 23 and the longitudinal axis of the portal sleeve 11 to form a closed space for receiving tissue so as to set and hold the portal sleeve in place.

Figure 20:
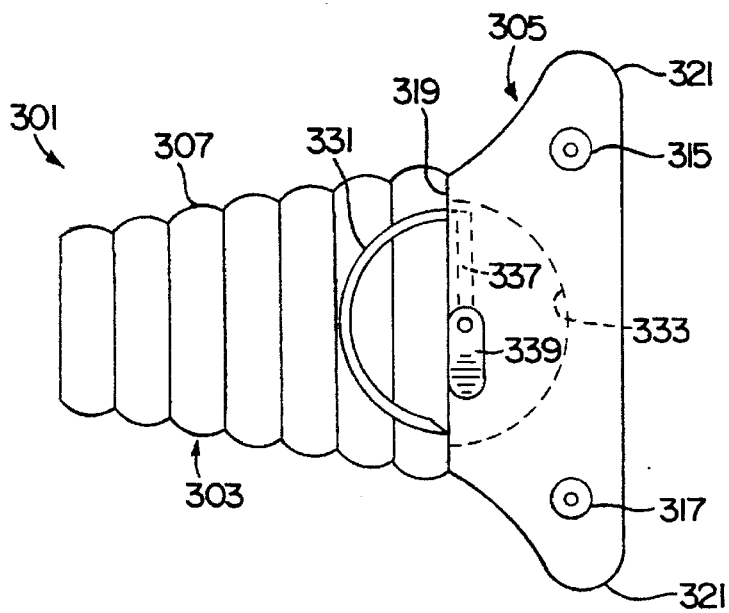
FIG. 20 is a top view of a further embodiment of a cannula anchoring system according to the present invention with needles mounted on a movable housing or stabilizer.
Figure 21:
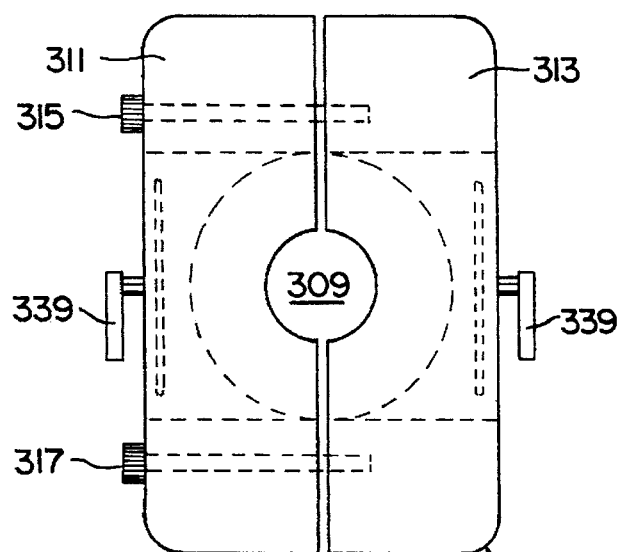
FIG. 21 is a rear view of the movable housing of FIG. 20.
Figure 22:
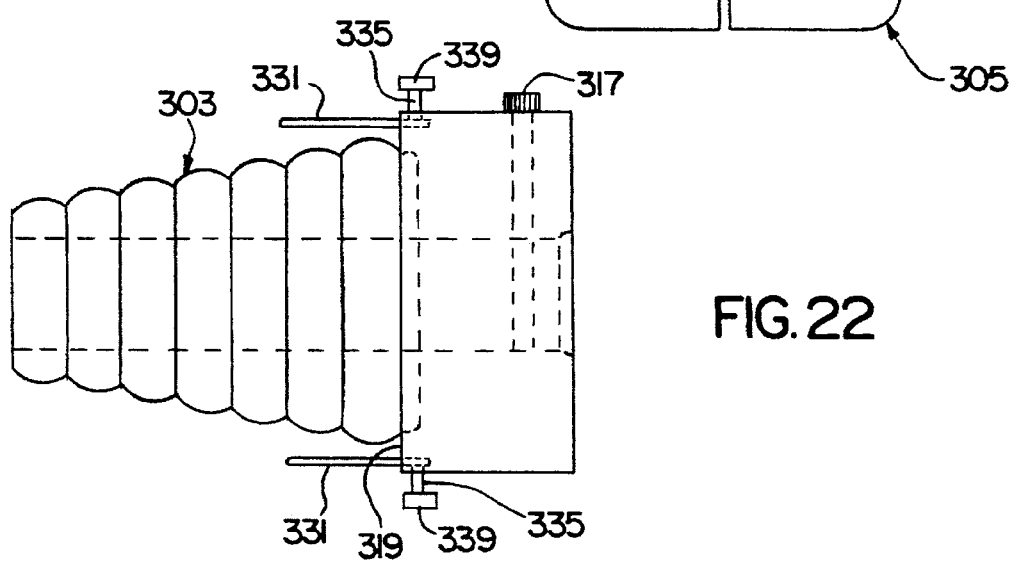
FIG. 22 is a side view of the cannula anchoring system of FIG. 20.

The anchoring system of the present invention can be used to stabilize cannulas in various types of anatomical cavities during various types of procedures. Depending on the nature of the procedure being performed and the characteristics of the anatomical cavity being penetrated, varying amounts of penetration of the cannula into the cavity may be required. Accordingly, as opposed to the cannula anchoring systems described above where the housing 21 is fixed to the cannula, a modification of the cannula anchoring system of the present invention is illustrated in FIGS. 20–22, wherein the anchoring needles are mounted on a housing movable along the cannula, such as on a stabilizer 301 having a configuration to be selectively positionable along the length of the portal sleeve 11 to engage the cavity wall at and/or in the puncture site. The stabilizer 301 includes a generally frusto-conical plug wall 303 for engaging the puncture site and a base 305, supported on a proximal end of the plug, from which needles 331 are deployed. A plurality of tissue engaging ribs 307 are formed on an exterior surface of the stabilizer along the length of the plug 303 to serve as tissue engaging protrusions and can be of any suitable configuration such as screw threads or, as shown, annular rings. A central lumen 309 extends longitudinally through both the plug 303 and the base 305 and is configured to slidably receive the portal sleeve 11. The base 305 includes opposed jaws 311 and 313 held in spaced relation by bolts 315 and 317 extending through holes formed in one jaw 311 and received in threaded receptacles in the other jaw 313. The jaws 311 and 313 are conformably shaped to define a distal face 319 abutting the proximal end of the plug 303 and extending laterally outward therefrom to establish exposed surfaces on opposite sides of the plug 303. From the distal face 319, the jaws 311 and 313 flare arcuately outward to form rounded shoulders 321 adjacent a proximal face of the base 305. Anchoring needles 331 are movably disposed on opposite sides of the plug 303 within needle pockets 333 at the distal face 319 of the base 305. The needles 331 are essentially the same as needles 31, each having a sharp tip at a distal end thereof and a proximal end connected with a radial arm 337. Rotatable shafts 335 are connected perpendicularly to the radial arms 337 coaxial with the needles 331 and are supported by the jaws 311 and 313, respectively. A radially extending handle 339 is secured perpendicular to each shaft 335 externally of the jaws 311 and 313 for rotation of the shaft 335, radial arm 337 and needle 331. The plug 303 of stabilizer 301 can be inflatable with ribs 307 reinforced within an elastic or distensible membrane having a length to extend partially or entirely through the thickness of the cavity wall whereby the plug can be inflated to engage the cavity wall after insertion.

Figure 23:
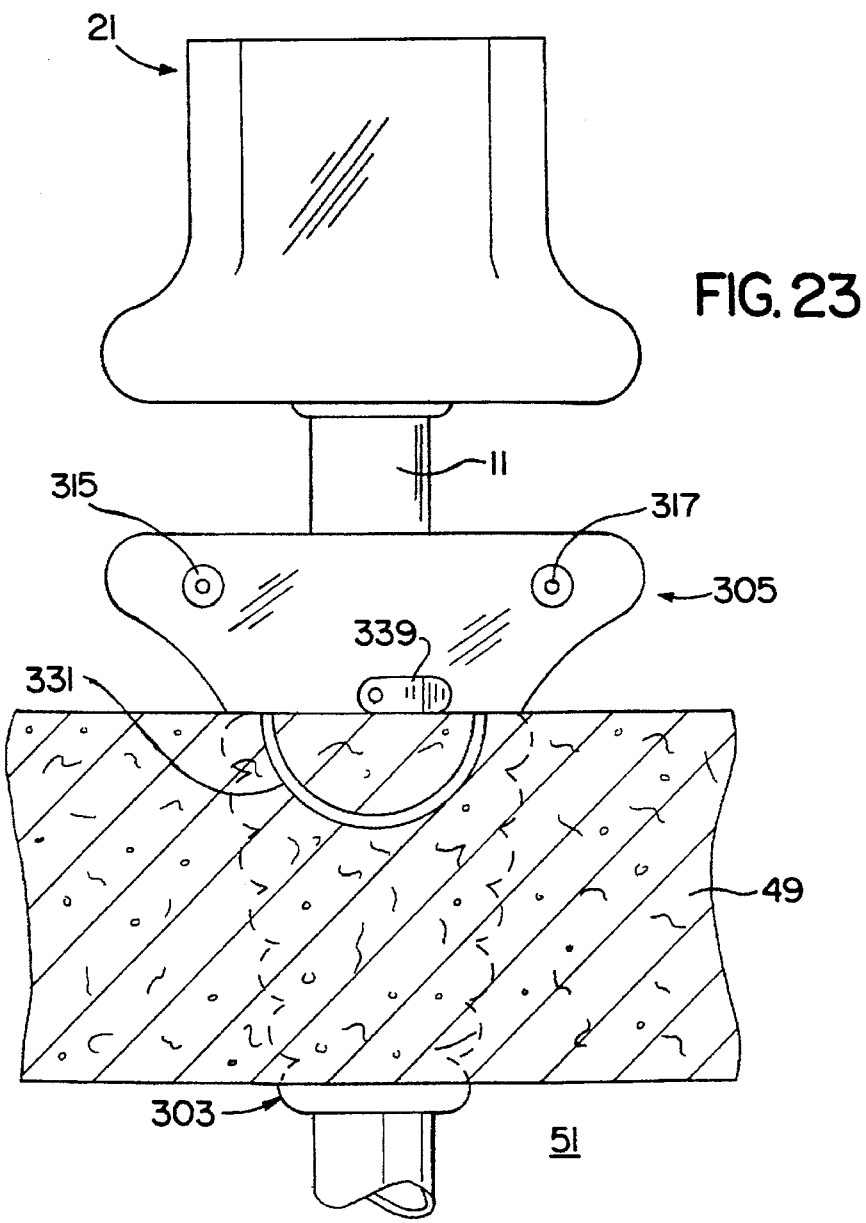
FIG. 23 is a broken view, partly in section, illustrating use of the cannula anchoring system of FIG. 20.

In use, the portal sleeve 11 is slidably disposed within the stabilizer 301 prior to puncture and penetration of the wall 49 of the anatomical cavity 51. After the wall of the anatomical cavity is punctured and the portal sleeve 11 inserted through the puncture site into the cavity, the base 305 of the stabilizer 301 is grasped and urged distally toward the cavity wall 49 so that the plug 303 slides over the portal sleeve 11 into the puncture site until the distal face 319 of the base 305 is adjacent the cavity wall 49. With the base 305 adjacent the cavity wall 49, the anchoring needles 331 are moved from retracted positions within the base 305 by turning each handle 180° in order that the needles may penetrate into the surrounding tissue as shown in FIG. 23. During penetration, the sharp distal end of each needle 331 is displaced through the opening formed in the distal face 319 of the base 305 and into the cavity wall. In the fully extended position, the needles 331 capture tissue between the arcuate body of the needle and the distal face 319 of the base thereby anchoring the base in position. The amount of portal sleeve protruding into the anatomical cavity may be adjusted by retracting or advancing the portal housing 21 externally of the anatomical cavity until a desired depth is achieved. With the portal sleeve 11 positioned as desired, the jaws 311 and 313 of the base are drawn together by tightening the bolts 315 and 317 so as to clamp the base 305 around the portal sleeve 11.

Removal or repositioning of the portal sleeve 11 is easily accomplished by loosening the bolts 315 and 317 which fasten the jaws 311 and 313 of the base together so that the portal sleeve 11 may slide within the central lumen 309 defined between the jaws. Once the portal sleeve 11 has been repositioned, the bolts 315 and 317 may once again be tightened so that the jaws 311 and 313 of the base are clamped around the portal sleeve 11 to prevent unintentional movement thereof.

Figure 24:
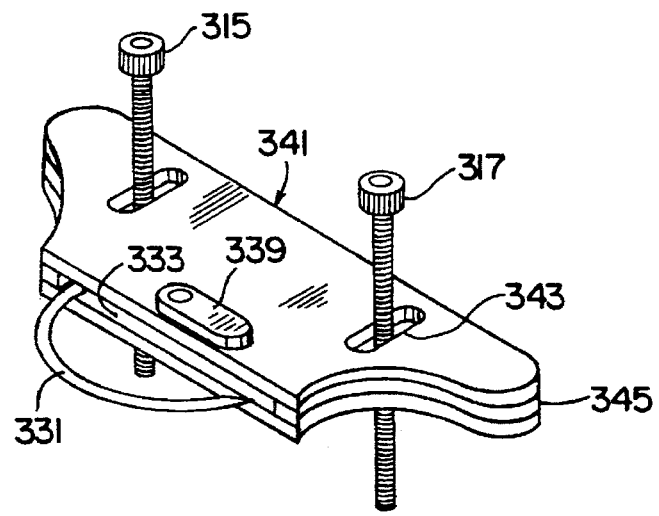
FIG. 24 is a perspective view of a detachable plate for use in a cannula anchoring system according to the present invention.
Figure 31:
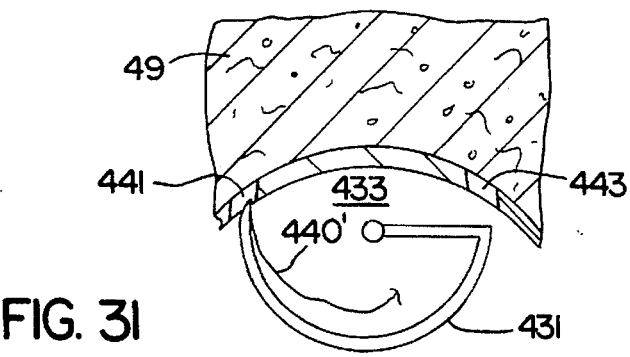
FIGS. 31–35 are fragmentary views, partly in section, illustrating use of the anchoring system of FIG. 25 for anchoring and puncture site closure.

A modification of the base 305 is shown in FIG. 24 in which a removable plate 341 is provided for attachment to the base. The plate 341 houses an anchoring needle 331 within a slot-like pocket 333 configured to receive the needle and is provided with a pair of spaced elongate openings 343 in flared shoulders 345 for passage of the bolts 315 and 317 therethrough. As a consequence of providing the elongate openings 343, the position of the plate 341 is adjustable in proximal and distal directions relative to the base 305 and the stabilizer. It will be appreciated that such plates could also be attached to a fixed housing on opposite sides of the portal sleeve to provide anchoring of the portal sleeve.

In another modification of the anchoring system of the present invention, anchoring needles are disposed directly within a housing in the form of a stabilizer 401, as shown in FIG. 25, including a central lumen 409 defined by a tubular wall 404 and a tissue engaging exterior plug surface defined by a generally frusto-conical side wall 403 provided with a plurality of ribs 407 along its length. Proximal and distal end walls 411 and 413 connect the inner tubular wall 404 with the exterior frusto-conical wall 403 to define one or more tapered cavities or needle-receiving pockets 433 therebetween. One or more needle assemblies are housed in the stabilizer, four equally angularly spaced needle assemblies being shown; and, each needle assembly includes an elongate shaft 435 mounted between proximal and distal end walls 411 and 413 of the stabilizer 401 and carrying a plurality of arcuate needles 431 of decreasing diameter along its length. The needles 431, which are essentially the same as needles 31, each include a sharp tip at a distal end 432 and a proximal end 434 connected to a radial arm 437 extending perpendicularly from the elongate shaft 435. The elongate shaft 435, radial arms 437 and needles 431 can be hollow, as shown in FIGS. 25 and 27, to provide a passageway for lengths of suture material 440 such that the lengths of suture material 440 run through the shaft and then each runs through an individual needle 331, or lengths of suture material 440' can be attached near the sharp distal ends 432 of each needle, as shown in FIG. 28 and in dashed lines in FIG. 25. As will be appreciated from the following, the number of lengths of suture material 440 and 440' carried by the needles depends upon the cavity wall being punctured, and a length of suture material need not be carried by each needle. Similarly, the number of needles will vary dependent upon the cavity wall being punctured as will the longitudinal spacing between adjacent needles and the radius of curvature thereof. The elongate shaft 435 is suspended between proximal and distal end walls 411 and 413 at an oblique angle relative to the longitudinal axis of the stabilizer 401 near the exterior tissue engaging wall 403. In a retracted position, shown in FIG. 29, the needles 431 are disposed within the cavity 433 defined between the exterior tissue engaging wall 403 and the inner tubular wall 404. A pair of openings 441 and 443 are formed in the exterior tissue engaging wall 403 in alignment with each of the needles 431, as shown in FIG. 30. Opening 441 of each pair is arranged adjacent the sharp distal end 432 of a corresponding needle held within the cavity to act as an exit permitting the distal end of the corresponding needle to pass out of stabilizer 401. The other opening 443 of each pair is circumferentially spaced from opening 441 to receive the sharp tip of the needle when it is rotated slightly more than 180° from the retracted position within the cavity 433 to act as an entrance permitting the distal end of the corresponding needle to pass into the stabilizer. Each of the needles is rotatable in a plane including the pair of openings 441 and 443 associated therewith, and the planes can be parallel or askew, the orientation and number of needles normally being determined by layers of tissue in a particular cavity wall being punctured.

Figure 32:
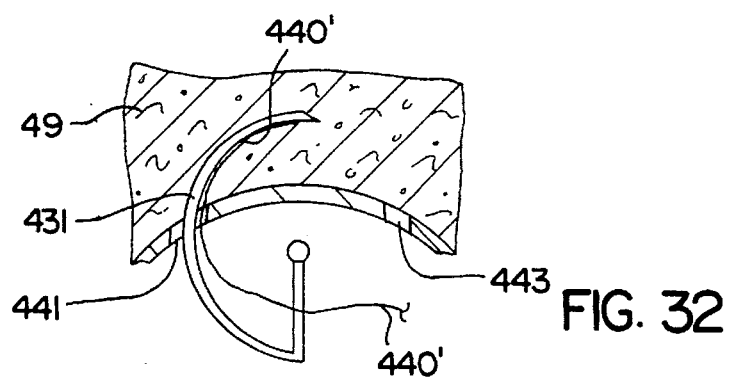
Figure 33:
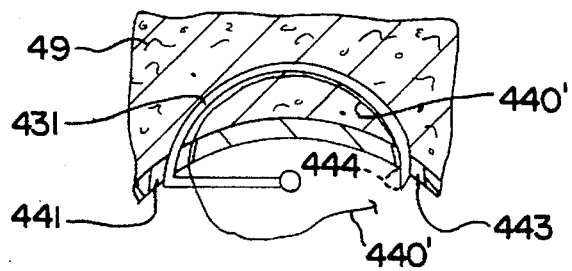
Figure 34:
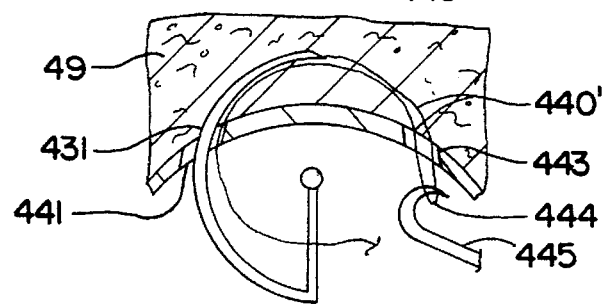
Figure 35:
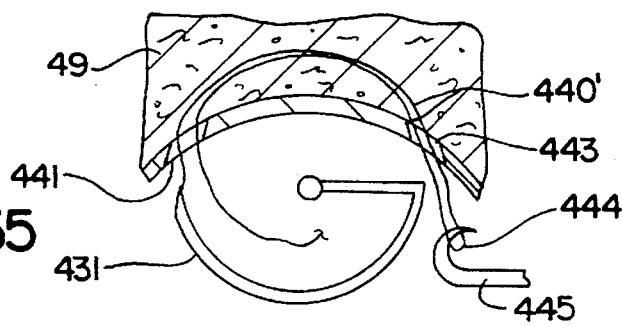

FIGS. 31–35 illustrate the use of the anchoring system of FIG. 25 to anchor a portal sleeve within a cavity wall during an endoscopic procedure and to facilitate puncture site closure following the procedure. The stabilizer 401 is moved along the portal sleeve into the cavity wall 49 and is then held to the portal sleeve by set screws or other frictional engagement, not shown such that, with the needles retracted within cavity 433, as shown, in FIG. 31, the stabilizer is positioned within the puncture site through a thickness of the cavity wall 49. Once positioned within the cavity wall 49, the elongate shafts 435 are rotated via handle 439 to move the anchoring needles 431 from the retracted positions within the cavities 433, through the exit openings 441 defined in the exterior tissue engaging wall 403 to penetrate the surrounding tissue of the anatomical cavity wall 49 as shown in FIG. 32. A length of suture material 440', attached near the sharp distal end 432 of the needle is carried along with the tip of the needle through the cavity wall 49 and back into the stabilizer 401 through the entrance of opening 443 as shown in FIG. 33 once the handle has been rotated 90°. With the needles 431 fully extended as shown, tissue is captured between the arcuate body of the needle and the exterior tissue engaging side wall 403 of the stabilizer thereby anchoring the stabilizer 401 and the portal sleeve within the cavity wall 49. Adjustment of the stabilizer and the portal sleeve can be accomplished by returning the needles to the retracted positions, repositioning the stabilizer and portal sleeve and then redeploying the needles. Once the tips 432 have entered the cavities 433 through openings 443, the distal ends of lengths of suture material 440' will be positioned within the cavities 433; and, once the needles are slightly backed away from the fully extended positions, loops 444 will be formed as shown in dashed lines in FIG. 33 due to frictional engagement of the lengths of suture material with the tissue of the cavity wall. Accordingly, once the procedure is completed, loops 444 are formed by slight reverse rotation of handles 439, and a hooked grasping implement 445 is inserted in the cavities to grab the loops 444 of the suture material 441 near the distal ends 432 of the needles from within the stabilizer. With the lengths of suture material 440' held at loops 444 as shown in FIG. 34, the needles are retracted from the extended positions back into the needle cavity 433 leaving a double length of suture material embedded in the cavity wall as shown in FIG. 35. The portal sleeve can be withdrawn from the cavity and the stabilizer before or after loops 444 are hooked or grasped; and, when the loops 444 are hooked first, the stabilizer can be withdrawn simultaneously with the portal sleeve or after the portal sleeve is withdrawn. The hooked loops 444 can be withdrawn simultaneously with the stabilizer or prior to withdrawal of the stabilizer; and, since the loops 444 will always be located adjacent an entrance opening 443, a mechanism can be positioned within the cavities at each opening 443 as part of the stabilizer to hook or grasp the loops 444. Upon withdrawal of the stabilizer 401 and the loops 444 from the cavity wall the lengths of suture material 440' are cut distally of the stabilizer, and the lengths of suture material remaining in the tissue of the cavity wall are drawn together to close the puncture site using conventional knotting techniques.

When the lengths of suture material 440 are passed through hollow needles 431, the puncture site closure is essentially the same as described above with the exception that the distal ends of the lengths of suture material must be grasped once they pass out of the tips of the needle, for example by forcep-like opposed jaws. The lengths of suture material 440 can pass through shafts 435 or can enter the proximal ends of the needles through openings at the proximal ends 434, and the lengths of suture material 440 and 440' can be supplied from an external position to the stabilizer through shafts 435 or openings in end wall 411 or can be supplied from spools within the cavities 433 within the stabilizer as shown at S in FIG. 25 in dashed lines for lengths of suture material 440'.

Figure 36:
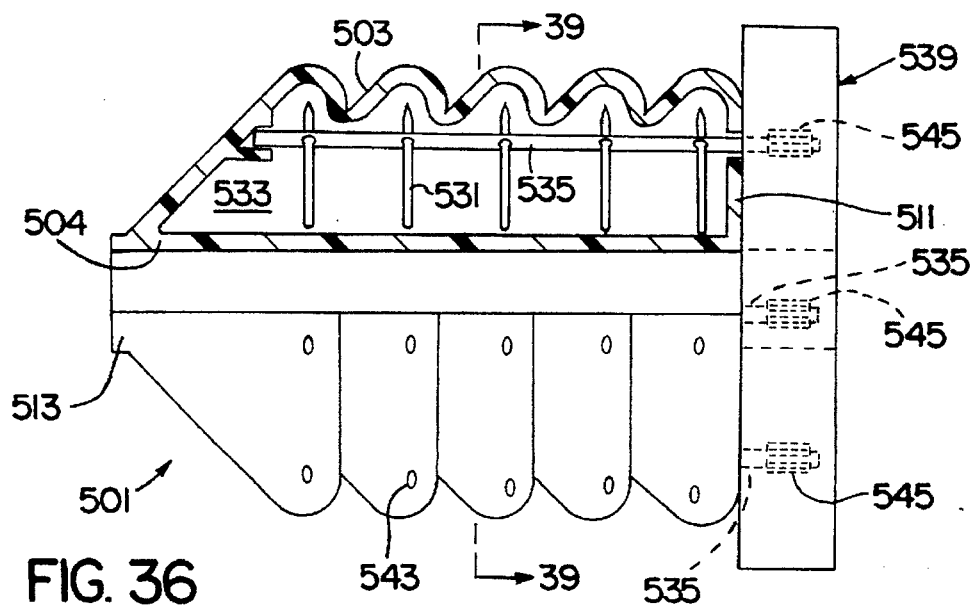
FIG. 36 is a side view, partly in section, showing another modification of a cannula anchoring system according to the present invention facilitating puncture site closure.
Figure 37:
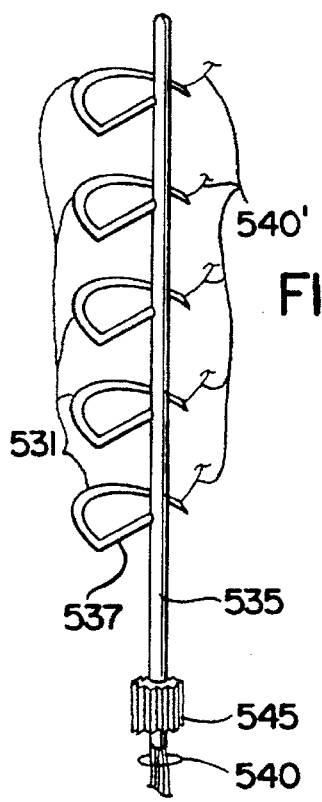
FIG. 37 is a perspective view of the needle assembly of the anchoring system of FIG. 36.
Figure 38:
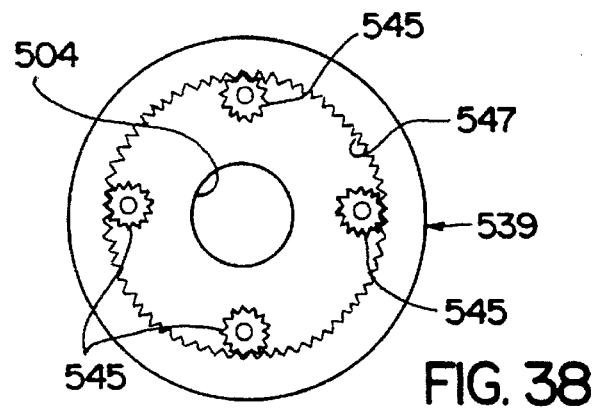
FIG. 38 is a proximal of the anchoring system of FIG. 36.
Figure 39:
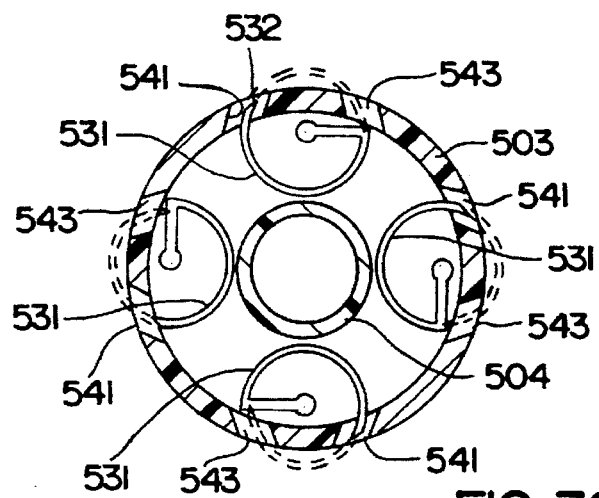
FIG. 39 is a cross-sectional view taken along line 39—39 of FIG. 36.

FIG. 36 shows a modification of the anchoring system of FIGS. 25–30 with the primary difference being the configuration of the stabilizer and the provision of a single mechanism for deploying the anchoring needles. The stabilizer 501 of FIG. 36 includes a generally tubular exterior tissue engaging side wall 503 supported externally of an inner tubular wall 504 to define an annular cavity 533 therebetween. Proximal and distal end walls 511 and 513 are connected between the exterior tissue engaging wall 503 and inner tubular wall 504 and support elongate shafts 535 of a plurality of needle assemblies substantially parallel to the longitudinal axis of the stabilizer 501, four equally angularly spaced needle assemblies being shown. The needle assemblies, as shown in FIG. 37, are essentially the same as those of FIG. 25 with the exception that shaft 535 supports a plurality of identically sized needles 531 and carries a gear 545 near a proximal end thereof. The gears 545 carried by each elongate shaft 535 proximal end wall 511 of the stabilizer 501 and are engaged by a circular ring gear 547 formed within a handle 539 rotatably mounted on the stabilizer as shown in FIG. 38. Rotation of the handle 539 and, the ring gear 547 causes rotation of gears 545 and shafts 535 to simultaneously rotate the needles 531 for deployment in a manner similar to that described with respect to the anchoring system of FIG. 25 and as indicated by dashed lines in FIG. 39. That is, when handle 539 is rotated counter clockwise looking at FIG. 38, needles 531 of each needle are moved from the retracted positions to the extended positioned (clockwise looking at FIG. 39) such that the sharp distal end tips 532 move through exit openings 541 in wall 507, through the tissue of the cavity wall and into the entrance openings 543 to capture the tissue of the cavity wall, pairs of circumferentially spaced exit and entrance openings 541 and 543 being aligned with each needle 531 in a manner similar to openings 441 and 443 in the anchoring system of FIG. 25. Lengths of suture material 540' can be attached adjacent the tips 532 of the needles, or lengths of suture material 540 can pass through the needles in the manner described above with respect to the anchoring system of FIG. 25, and the lengths of suture material can be grasped or hooked in a similar fashion to close a puncture site after the stabilizer 501 is withdrawn therefrom.

Figure 40:
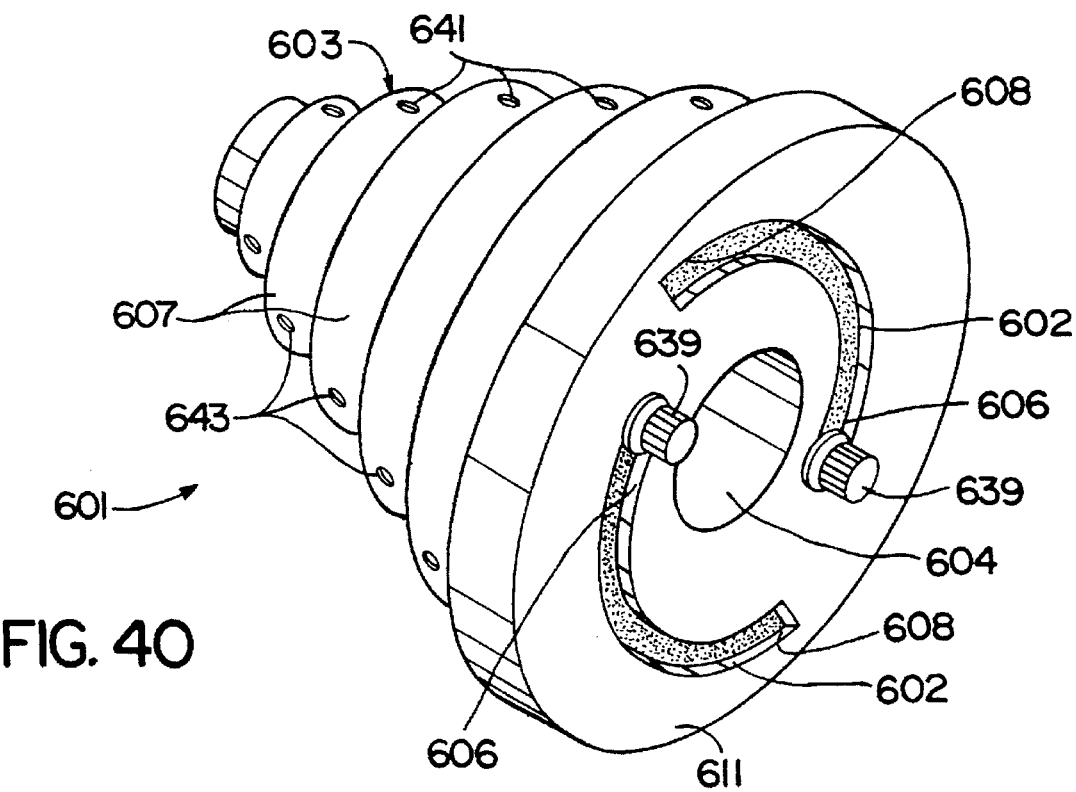
FIG. 40 is a perspective view of another cannula anchoring system according to the present invention facilitating puncture site closure.
Figure 41:
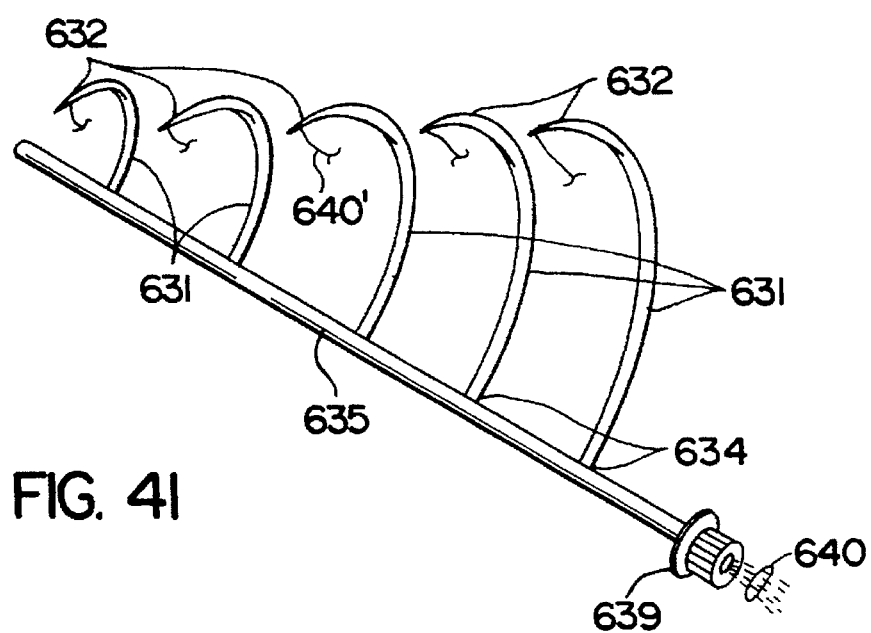
FIG. 41 is a perspective view of the needle assembly of the anchoring system of FIG. 40.

In a further modification, a stabilizer 601, shown in FIG. 40, has arcuate slots 602 formed in a proximal face or end wall 611 of the stabilizer to support proximal ends of elongate shafts 635 which terminate at handles 639. A pair of opposed needle assemblies, each including a plurality of arcuate needles 631 having sharp distal ends 632 and proximal ends 634 connected to an elongate shaft 635, as shown in FIG. 41, are housed within a cavity 633 defined between an exterior tissue engaging wall 603 with ribs 607 and an inner tubular wall 604 of the stabilizer 601. The arcuate slots 603 curve between inner ends 606 and outer ends 608 with inner ends 606 disposed radially closer to the longitudinal axis through the stabilizer defined by the lumen of inner tubular wall 604 than outer ends 608 such that movement of handles 639 along the tracks formed by slots 602 causes the needle to move outwardly from the retracted positions within the stabilizer. Exterior wall 603 has circumferentially spaced exit openings 641 and entrance openings 643 similar to the anchoring systems of FIGS. 25 and 36, and angled ramps 642 are disposed adjacent exit openings 641 to direct the needles outwardly from the stabilizer upon deployment.

Figure 42:
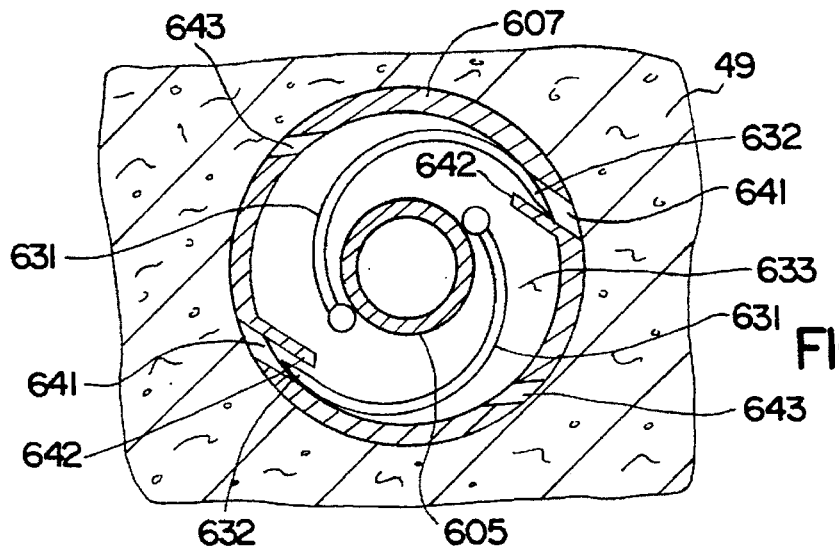
FIGS. 42–44 are cross-sectional views illustrating use of the anchoring system of FIG. 40 for anchoring and puncture site closure.
Figure 43:
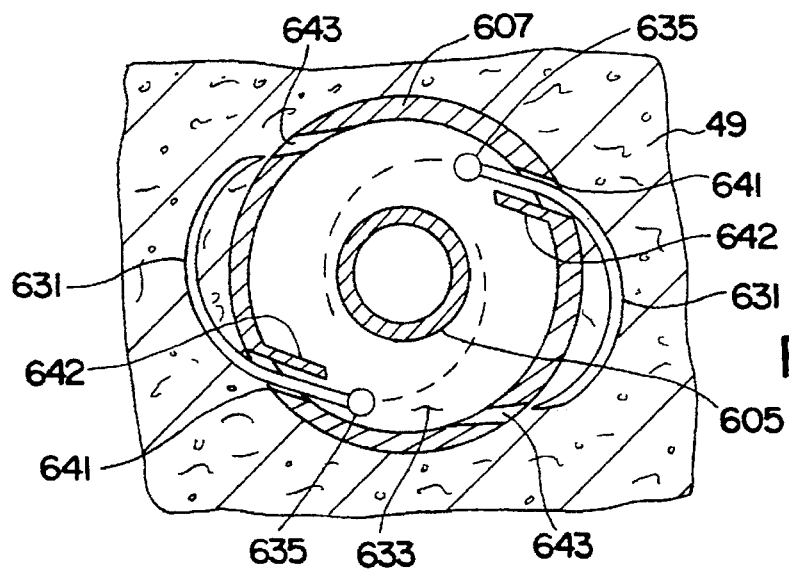
Figure 44:
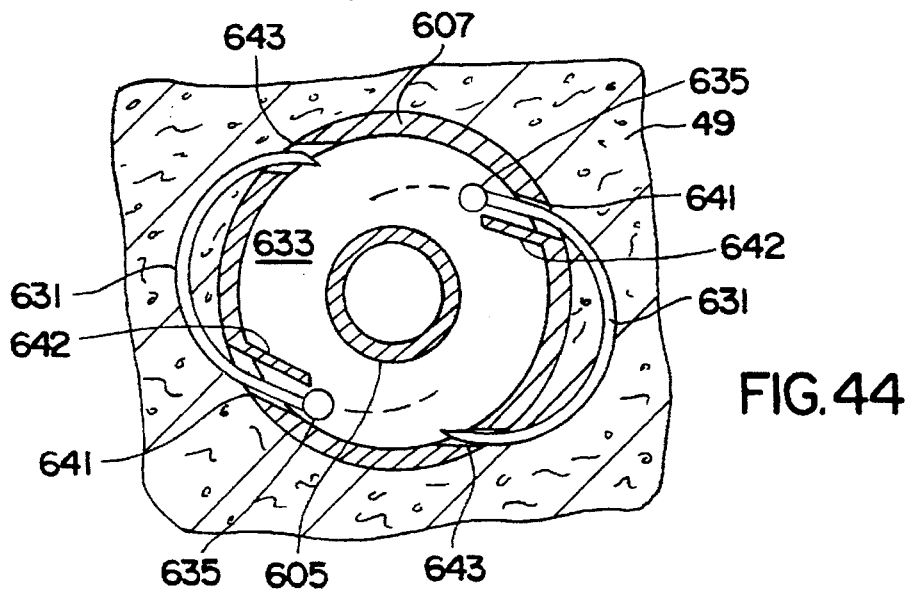

In a retracted position, the anchoring needles 631 are disposed within the cavity 633, as shown in FIG. 42, and translation of the elongate shafts 635 in the slots 602 moves the anchoring needles 631 along outwardly spiraling paths within the cavity 633 to extend from the stabilizer through openings 641 to penetrate the surrounding tissue as shown in FIG. 43 under the influence of ramps 642 which protrude inwardly sufficiently to extend inwardly beyond the sharp tips 632 of the needles when the needles are in the retracted position. With the elongate shafts 635 translated completely to the opposite outer ends of the arcuate slots 602, the needles loop back into the stabilizer through entrance openings 643 in the outer tissue engaging wall 603, as shown in FIG. 44. Hence, the stabilizer and portal sleeve passing therethrough are anchored to the cavity wall 49, and by attaching lengths of suture material 640' to the distal ends 632 of the needles or passing lengths of suture material 640 through the needles, puncture site closure can be accomplished in essentially the same manner as previously described with respect to the anchoring systems of FIGS. 25 and 36 since the lengths of suture material can be grasped or hooked within cavity 633.

Another modification of the anchoring system of the present invention is shown in FIG. 45, wherein a plurality of anchoring needles 731 are formed integrally with a portal sleeve 711. The anchoring needles 731 are defined by cuts 701 and 703 made in the portal sleeve 711 intermediate proximal and distal ends of the sleeve. The cuts 701 and 703 are substantially longitudinal and made to intersect at a point distally spaced from a proximal end to define a narrow strip of material therebetween having a sharp distal end. The strip of material can be treated using heat setting techniques to form outwardly extending needles 731 which terminate in sharp tips at distal ends 732 thereof. As a consequence of the treatment, the needles 731 are resiliently biased in the extended position shown in FIG. 46. A frusto-conical plug stabilizer 705 is slidably disposed on the portal sleeve 711 distally of portal housing 21 and is normally proximal of the anchoring needles 731 when deployed in extended positions. Translation of the frusto-conical plug 705 over the integrally formed needles 731, as shown in FIG. 47, forces the radially extending needles 731 to retract back into retracted positions flush with the portal sleeve 711.

Figure 48:
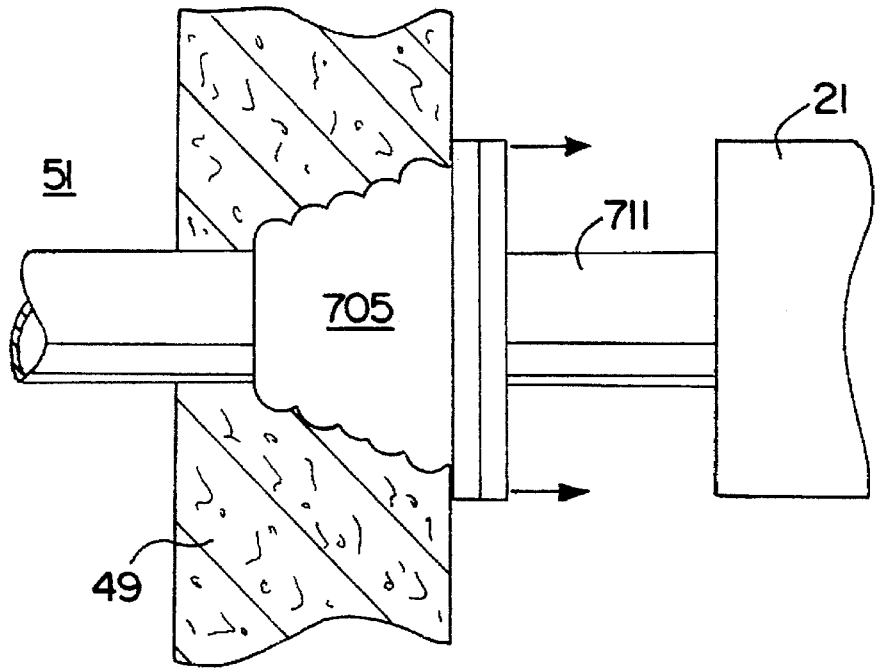
Figure 49:
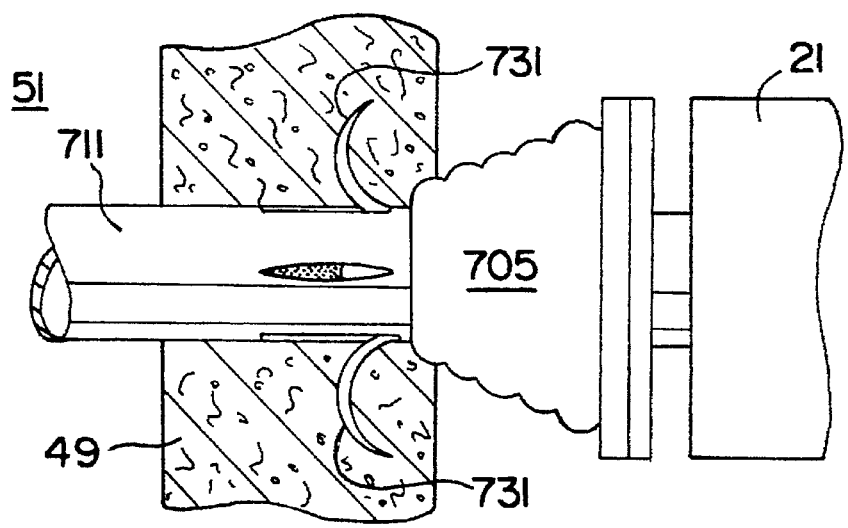

In use, the stabilizer 705 and portal sleeve 711 are inserted into a cavity wall 49 as previously described, with the exception that the portion of the portal sleeve 711 having the integral needles 731 formed therein is positioned intermediate the cavity wall 49 within stabilizer 705, as shown in FIG. 48. The stabilizer 705 is then retracted proximally from the cavity wall while maintaining the position of the portal sleeve 711, resulting in outward deployment of the integral needles 731 as shown in FIG. 49 such that the portal sleeve 711 is anchored to the cavity wall.

From the above, it will be appreciated that the anchoring system of the present invention can be used for stabilization, manipulation and puncture site closure as well as for longitudinally holding a cannula relative to a cavity wall. For puncture site closure, the needles are positioned within the cavity wall to penetrate the tissue from the inside and are preferably combined with a stabilizer member in a manner such that lengths of suture material can be passed through one or more layers of a cavity wall via the needles and, after removal of the stabilizer member and the grasped or hooked ends of the lengths of suture material, the lengths of suture material can be drawn together and knotted to close the puncture site by layer-by-layer suturing.

Although arcuate and straight needles have been illustrated and described herein for use in the anchoring system of the present invention, any suitably shaped needle for penetrating and holding the tissue of a cavity wall can be used. The needles can be positioned directly on a cannula or on any structure carried by a cannula. The needles can be made of any medically-acceptable material for penetrating tissue, such as stainless steel or bioabsorbable materials. The needles can have smooth, irregular or any other type of surface, can be of any cross-sectional shape, and be completely solid, hollow, or any combination of the two. When hollow, the needles can be advantageously used to inject medicaments, such as anesthetics or antibiotics, into the tissue of the cavity wall surrounding a puncture site. Any of the needles described herein can be biased toward the retracted and/or extended positions; and, while spring-loaded detents and protrusions have been described for holding the needles in desired positions, any mechanism for locking the needles in place can be employed. Various operating mechanisms can be coupled with the tissue penetrating members for moving the tissue penetrating members between the retracted and extended positions to anchor the cannula to the cavity wall and to release the cannula with the rotating, pivoting, sliding and arcuately moving operating handles disclosed herein being exemplary. However, it is noted that trauma is reduced where the operating mechanism includes a shaft rotatable or pivotal about an axis and the tissue penetrating members are arcuate needles having a center of curvature aligned with the axis of rotation of the shaft as disclosed herein in the above anchoring systems incorporating curved needles since the needles are constrained to follow a single curved path in the tissue during entry into and removal from the cavity wall.

The use of tissue penetrating members, such as needles, for anchoring a cannula in a cavity wall is particularly advantageous since the tissue penetrating members are located adjacent the puncture site thereby permitting additional functions to be accomplished. For example, deployment of the tissue penetrating members pulls or draws the surrounding tissue toward the cannula to enhance sealing therearound, particularly when needle arrangements similar to FIGS. 18, 25, 36 and 40 are used or the direction of movement of the needles of FIGS. 1, 12 and 13 are reversed such that the needle distal ends or tips move toward the cannula as shown by needles 131' in dashed lines in FIG. 15. The sealing function is extremely helpful for large incision procedures where the cannula or other portal is substantially smaller than the incision or puncture site in that the surrounding tissue can be gathered and held in place by the needles. Additionally, lifting of a cavity wall is facilitated by engaging the external surface or the thickness of the cavity wall, particularly in conjunction with expandable devices for engaging the internal surface of the cavity wall, such as balloons or mushroom hinges. Furthermore, by using hollow anchoring needles, medicaments can be precisely administered to the tissue at the puncture site; and, thus, the anchoring needles in any of the anchoring systems according to the present invention can be hollow to permit medicaments or fluids to pass therethrough in either direction as well as to permit passage of suture material therethrough. When the anchoring needles are used to provide the additional function of facilitating puncture site closure, for example, as illustrated by the anchoring systems of FIGS. 25, 36 and 40, lengths of suture material can be precisely passed through desired tissue layers of a cavity wall or at desired depths in a cavity wall. The radius of curvature and the circumferential length of the anchoring needles when also used for puncture site closure can be selected in accordance with the particular cavity wall being punctured, for example from 90° to 360°, and the stabilizer can be configured such that the suture material distal ends or loops formed in the stabilizer adjacent the entrance openings can be accessible after the portal sleeve is withdrawn via the central lumen in the stabilizer.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A cannula anchoring system comprising:
   a cannula adapted to be inserted through a wall of an anatomical cavity and having a lumen for communication with the anatomical cavity;
   a tissue penetrating member carried by said cannula at a position adjacent the cavity wall when said cannula is inserted through the cavity wall, said tissue penetrating member having a sharp distal end and being movable between a retracted position where said sharp distal end is non-exposed and an extended position where said sharp distal end is exposed; and
   an operating mechanism coupled with said tissue penetrating member and operable to move said tissue penetrating member between said retracted and extended positions whereby said sharp distal end of said tissue penetrating member can be moved to penetrate the cavity wall to anchor said cannula therein.

2. A cannula anchoring system as recited in claim 1 and further comprising a plurality of said tissue penetrating members.

3. A cannula anchoring system as recited in claim 2 wherein said tissue penetrating members are resilient needles integrally formed with said cannula and said operating mechanism includes a stabilizer slidable along said cannula to move said needles between said retracted and extended positions.

4. A cannula anchoring system comprising:
   a cannula adapted to be inserted through a wall of an anatomical cavity and having a lumen for communication with the anatomical cavity;
   a tissue penetrating member carried by said cannula at a position adjacent the cavity wall when said cannula is inserted through the cavity wall, said tissue penetrating member being movable between a non-exposed, retracted position and an exposed, extended position;
   an operating mechanism coupled with said tissue penetrating member and operable to move said tissue penetrating member between said retracted and extended positions whereby said tissue penetrating member can be moved to penetrate the cavity wall to anchor said cannula therein; and
   a housing coupled with said cannula wherein said tissue penetrating members are needles having sharp distal ends and said sharp distal ends are disposed within said housing when said needles are in said retracted positions.

5. A cannula anchoring system as recited in claim 4 wherein each of said needles has a proximal end and a body disposed between said sharp distal end and said proximal end and further comprising recess means for receiving said sharp distal ends of said needles when said needles are in said extended positions to form closed spaces capturing tissue of the cavity wall therein.

6. A cannula anchoring system as recited in claim 5 wherein said cannula has a proximal end and said housing is fixed to said proximal end of said cannula.

7. A cannula anchoring system as recited in claim 6 wherein said housing has a front wall and a pair of opposed flared wings adjacent said front wall and said needles are disposed within said flared wings in said retracted positions.

8. A cannula anchoring system as recited in claim 5 wherein said housing is slidable along said cannula.

9. A cannula anchoring system as recited in claim 4 wherein each of said needles has a proximal end and an arcuate body disposed between said sharp distal end and said proximal end, said arcuate body having a center of curvature and wherein said operating mechanism includes shaft means connected with said proximal ends of said needles and rotatable about an axis aligned with said centers of curvature of said needles for rotating said needles between said retracted and extended positions.

10. A cannula anchoring system as recited in claim 9 wherein said shaft means includes a single shaft for rotating a plurality of said needles.

11. A cannula anchoring system as recited in claim 9 wherein said shaft means includes a plurality of shafts each connected with at least one of said needles.

12. A cannula anchoring system as recited in claim 9 wherein said needles rotate in a single plane.

13. A cannula anchoring system as recited in claim 9 wherein at least two of said needles rotate in transverse planes.

14. A cannula anchoring system as recited in claim 9 wherein at least two of said needles rotate in spaced parallel planes.

15. A cannula anchoring system as recited in claim 9 wherein at least one of said needles rotates in a first plane, and at least one of said needles rotates in a second plane disposed at an angle relative to said first plane.

16. A cannula anchoring system as recited in claim 4 wherein said housing includes an outer wall for engaging the cavity wall along the thickness thereof and a lumen for receiving said cannula, said outer wall having an exit opening aligned with each of said needles to permit said needles to move from said retracted position into the thickness of the cavity wall to said extended position.

17. A cannula anchoring system as recited in claim 16 wherein said outer wall has an entrance opening circumferentially spaced from each of said exit openings to receive said distal ends of said needles to capture tissue of the cavity wall between said needles and said housing when said needles are fully moved to said extended positions.

18. A cannula anchoring system as recited in claim 17 wherein said needles are hollow and further comprising lengths of suture material passing through said needles and the tissue of the cavity wall into said housing through said entrance openings to permit suturing of the cavity wall after said cannula is withdrawn from the cavity wall.

19. An anchoring system as recited in claim 17 and further comprising lengths of suture material attached adjacent said sharp distal ends of said needles to follow said needles through the tissue of the cavity wall into said housing through said entrance openings to permit suturing of the cavity wall after said cannula is withdrawn from the cavity wall.

20. A cannula anchoring system as recited in claim 4 wherein said needles are hollow whereby medicaments or lengths of suture material can pass therethrough.

21. A method of anchoring a cannula in a cavity wall comprising the steps of:

inserting the cannula through a puncture site in the cavity wall at a desired angular orientation; and penetrating the tissue of the cavity wall adjacent the puncture site with sharp tissue penetrating members carried by the cannula to stabilize the cannula at the desired angular orientation.

22. A method of anchoring a cannula in a cavity wall comprising the steps of:

inserting the cannula through a puncture site in the cavity wall; and penetrating the tissue of the cavity wall adjacent the puncture site with sharp tissue penetrating members carried by the cannula wherein said penetrating step includes moving the tissue penetrating members from an unexposed retracted position to an exposed extended position in the tissue.

23. A method of anchoring a cannula in a cavity wall as recited in claim 22 wherein said penetrating step includes penetrating the external surface of the cavity wall.

24. A method of anchoring a cannula in a cavity wall as recited in claim 22 wherein said penetrating step includes penetrating the cavity wall along the thickness of the puncture site.

25. A method of anchoring a cannula in a cavity wall as recited in claim 24 and further comprising the steps of using the tissue penetrating members to pass lengths of suture material through the thickness of the cavity wall and drawing the cavity wall together via the lengths of suture material to close the puncture site.

26. A method of anchoring a cannula in a cavity wall as recited in claim 25 wherein said using step includes passing the lengths of suture material through the tissue penetrating members.

27. A method of anchoring a cannula in a cavity wall as recited in claim 25 wherein said using step includes attaching the lengths of suture material adjacent distal ends of the tissue penetrating members and pulling the lengths of suture material through the cavity wall with the tissue penetrating members.

* * * * *